United States Patent
Stark et al.

(10) Patent No.: US 7,291,011 B2
(45) Date of Patent: Nov. 6, 2007

(54) PLACING ORTHODONTIC OBJECTS ALONG AN ARCHWIRE WITHIN A THREE-DIMENSIONAL (3D) ENVIRONMENT

(75) Inventors: Nicholas A. Stark, Cottage Grove, MN (US); Richard E. Raby, North St. Paul, MN (US)

(73) Assignee: 3M Innovative Properties Company, St. Paul, MN (US)

(*) Notice: Subject to any disclaimer, the term of this patent is extended or adjusted under 35 U.S.C. 154(b) by 219 days.

(21) Appl. No.: 10/959,624

(22) Filed: Oct. 6, 2004

(65) Prior Publication Data

US 2006/0073435 A1    Apr. 6, 2006

(51) Int. Cl.
    *A61C 3/00* (2006.01)
(52) U.S. Cl. ..................................... 433/24
(58) Field of Classification Search .................. 433/24
    See application file for complete search history.

(56) References Cited

U.S. PATENT DOCUMENTS

| | | | |
|---|---|---|---|
| 5,879,158 A | 3/1999 | Doyle et al. | |
| 6,099,314 A | 8/2000 | Kopelman et al. | |
| 6,123,544 A | 9/2000 | Cleary | |
| 6,152,731 A | 11/2000 | Jordan et al. | |
| 6,318,994 B1 * | 11/2001 | Chishti et al. | 433/24 |
| 6,322,359 B1 | 11/2001 | Jordan et al. | |
| 6,334,772 B1 | 1/2002 | Taub et al. | |
| 6,334,853 B1 | 1/2002 | Kopelman et al. | |
| 6,457,978 B1 | 10/2002 | Cloonan et al. | |
| 6,632,089 B2 * | 10/2003 | Rubbert et al. | 433/24 |
| 6,664,986 B1 | 12/2003 | Kopelman et al. | |
| 6,695,613 B2 | 2/2004 | Taub et al. | |
| 6,697,164 B1 | 2/2004 | Babayoff et al. | |
| 6,739,869 B1 | 5/2004 | Taub et al. | |
| 7,029,275 B2 | 4/2006 | Rubbert et al. | |
| 7,033,327 B2 | 4/2006 | Raby | |
| 7,080,979 B2 | 7/2006 | Rubbert et al. | |
| 2002/0015934 A1 | 2/2002 | Rubbert et al. | |
| 2002/0150859 A1 * | 10/2002 | Imgrund et al. | 433/24 |

(Continued)

FOREIGN PATENT DOCUMENTS

WO    97/03622    2/1997

(Continued)

OTHER PUBLICATIONS

U.S. Appl. No. 10/734,323, "Method of Placing Orthodontic Brackets on Teeth in a 3D Virtual World," filed Dec. 12, 2003.

(Continued)

*Primary Examiner*—Cary E. O'Connor
(74) *Attorney, Agent, or Firm*—James D. Christoff

(57) ABSTRACT

A system automatically determines positions of orthodontic objects, such as teeth and/or orthodontic appliances, along an archwire within a three-dimensional (3D) environment based on a proposed orthodontic prescription. The resulting placement of the orthodontic objects in the dentition predicts a final occlusion that may result from the proposed orthodontic prescription. An orthodontic practitioner may interact with the system to enter a proposed orthodontic prescription, or the system may choose the proposed orthodontic prescription from a number of standardized prescriptions stored in a database. The system may also display a digital representation of the orthodontic objects at the determined positions. The practitioner may modify the proposed prescription and view the resulting placement of the orthodontic objects until a desired result is obtained.

31 Claims, 16 Drawing Sheets

U.S. PATENT DOCUMENTS

| | | | |
|---|---|---|---|
| 2002/0156652 A1* | 10/2002 | Sachdeva et al. | 705/2 |
| 2003/0003416 A1* | 1/2003 | Chishti et al. | 433/24 |
| 2003/0163291 A1* | 8/2003 | Jordan et al. | 703/1 |
| 2003/0215764 A1 | 11/2003 | Kopelman et al. | |
| 2003/0219692 A1 | 11/2003 | Kopelman et al. | |
| 2003/0224316 A1 | 12/2003 | Marshall | |
| 2004/0054304 A1 | 3/2004 | Raby | |
| 2004/0142297 A1 | 7/2004 | Taub et al. | |
| 2004/0142298 A1 | 7/2004 | Taub et al. | |
| 2005/0191593 A1* | 9/2005 | Knopp | 433/24 |

OTHER PUBLICATIONS

U.S. Appl. No. 10/771,641, "Planar Guides to Visually Aid Orthodontic Appliance Placement with a Three-Dimensional (3D) Environment," filed Feb. 4, 2004.

U.S. Appl. No. 10/903,686, "Automatic Adjustment of an Orthodontic Bracket to a Desired Occlusal Height Within a Three-Dimensional (3D) Environment," filed Jul. 30, 2004.

* cited by examiner

PLACING ORTHODONTIC OBJECTS ALONG AN ARCHWIRE WITHIN A THREE-DIMENSIONAL (3D) ENVIRONMENT

TECHNICAL FIELD

The invention relates to electronic orthodontics and, more particularly, computer-based techniques for assisting orthodontic diagnosis and treatment.

BACKGROUND

The field of orthodontics is concerned with repositioning and aligning a patient's teeth for improved occlusion and aesthetic appearance. For example, orthodontic treatment often involves the use of tiny slotted appliances, known as brackets that are fixed to the patient's anterior, cuspid, and bicuspid teeth. An archwire is received in the slot of each bracket and serves as a track to guide movement of the teeth to desired orientations. The ends of the archwire are usually received in appliances known as buccal tubes that are secured to the patient's molar teeth.

A number of orthodontic appliances in commercial use today are constructed on the principle of the "straight wire concept" developed by Dr. Lawrence F. Andrews, D.D.S. In accordance with this concept, the shape of the appliances, including the orientation of the slots of the appliances, is selected so that the slots are aligned in a flat reference plane at the conclusion of treatment. Additionally, a resilient archwire is selected with an overall curved shape that normally lies in a flat reference plane.

When the archwire is placed in the slots of the straight wire appliances at the beginning of orthodontic treatment, the archwire is often deflected upwardly or downwardly from one appliance to the next in accordance with the patient's malocclusions. However, the resiliency of the archwire tends to return the archwire to its normally curved shape that lies in a flat reference plane. As the archwire shifts toward the flat reference plane, the attached teeth are moved in a corresponding fashion toward an aligned, aesthetically pleasing array.

As can be appreciated, it is important for the practitioner using straight wire appliances to fix each bracket in the exact proper position on the corresponding tooth. If, for example, a bracket is placed too far in an occlusal direction on the tooth surface, the archwire will tend to position the crown of the tooth too close to the gingiva (gums) at the end of the treatment. As another example, if the bracket is placed to one side of the center of the tooth in either the mesial or distal direction, the resultant tooth orientation will likely be an orientation that is excessively rotated about its long axis.

The process of positioning and bonding the brackets to the patient's teeth requires considerable care, and requires the practitioner to visually determine the proper location of the brackets on the respective teeth. Often, in a technique known as indirect bonding, a practitioner determines bracket positions by the use of a ruler, protractor and pencil to measure and mark features on a plaster cast made from impressions of the patient's teeth. This process is often difficult to carry out with precision, and may be subjective in nature. Consequently, it is often difficult for the practitioner to ensure that the brackets are precisely positioned on the teeth at correct locations.

SUMMARY

In general, the system automatically determines positions of orthodontic objects (such as teeth and/or orthodontic appliances) along an archwire within a three-dimensional (3D) environment based on a proposed orthodontic prescription. An orthodontic practitioner may interact with the system to enter a proposed orthodontic prescription, or the system may choose the proposed orthodontic prescription from a number of standardized prescriptions stored in a database. The system may also display a digital representation of the teeth at the determined positions.

In one embodiment, the invention is directed to a method comprising automatically determining positions of orthodontic objects along an archwire within a three-dimensional (3D) environment based on a proposed orthodontic prescription, and displaying a digital representation of the orthodontic objects at the determined positions. In another embodiment, the invention is directed to a system comprising a computing device and modeling software executing on the computing device to provide a three-dimensional (3D) environment. The modeling software comprises a tooth packing control module that automatically determines positions of orthodontic objects along an archwire within a three-dimensional (3D) environment based on a proposed orthodontic prescription, and a user interface that displays a digital representation of the orthodontic objects at the determined positions.

In another embodiment, the invention is directed to a computer-readable medium containing instructions. The instructions cause a programmable processor to automatically determine positions of orthodontic objects along an archwire within a three-dimensional (3D) environment based on a proposed orthodontic prescription, and display a digital representation of the orthodontic objects at the determined positions. The details of one or more embodiments of the invention are set forth in the accompanying drawings and the description below. Other features, objects, and advantages of the invention will be apparent from the description and drawings, and from the claims.

DETAILED DESCRIPTION

Figure 1:
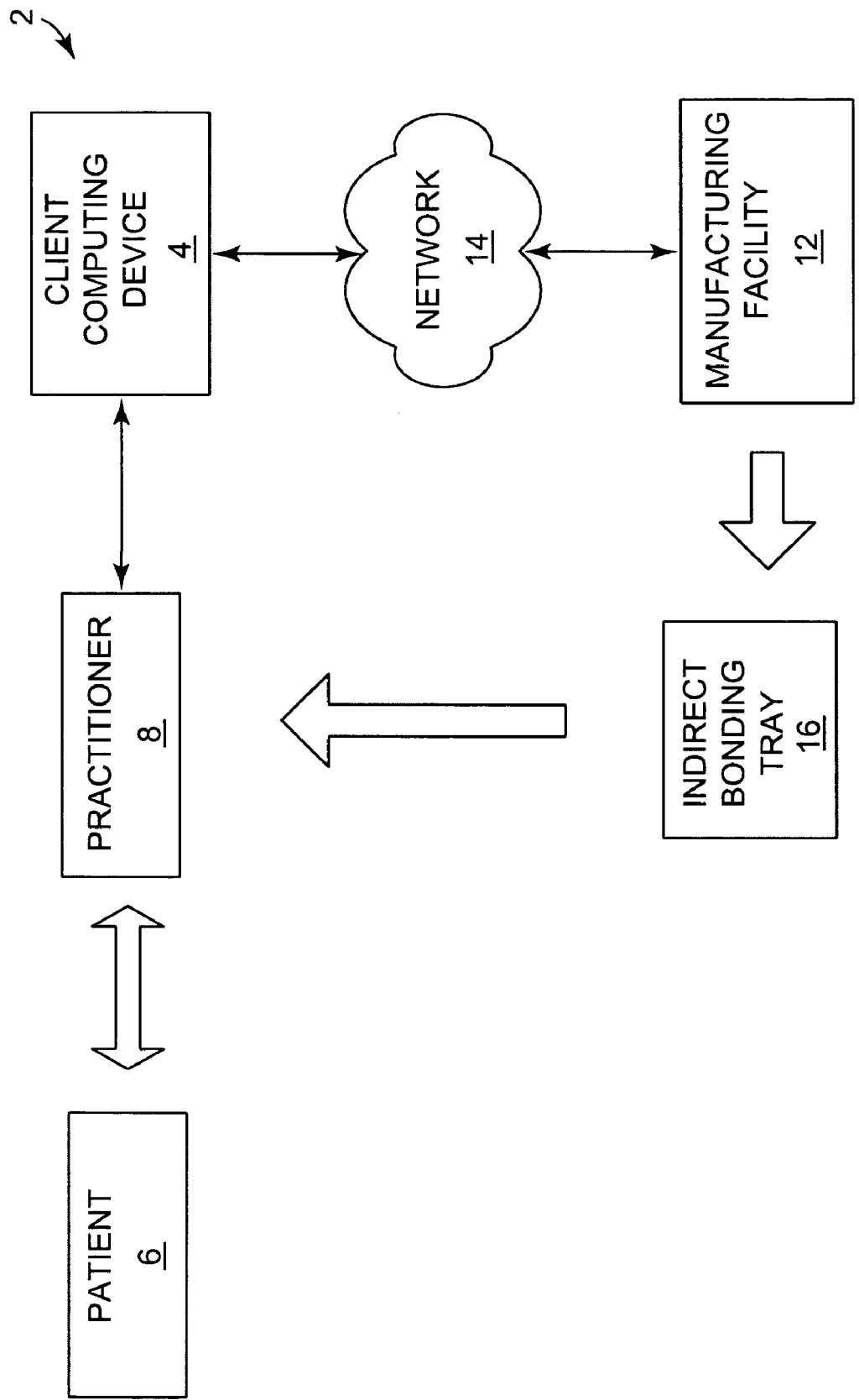
FIG. 1 is a block diagram illustrating an exemplary computer environment in which a client computing device automatically places orthodontic objects along an archwire.

FIG. 1 is a block diagram illustrating an exemplary computer environment 2 in which a client computing device 4 presents an environment for automatically determining positions of orthodontic objects, such as teeth and/or orthodontic appliances, along an archwire based on a proposed orthodontic prescription. The client computing device may also generate a three-dimensional (3D) representation of the orthodontic objects at the determined positions. Orthodontic practitioner 8 may interact with the system to enter a proposed orthodontic prescription, or, client computing device 4 may choose a proposed prescription from a number of standardized prescriptions stored in a database. The system thus allows the practitioner to visualize the final occlusion resulting from the proposed orthodontic prescription at the conclusion of treatment.

Visualization of the teeth at the determined positions enables the practitioner to determine whether the proposed orthodontic prescription will achieve an acceptable functional and/or aesthetic result. The practitioner may decide, based on the displayed final occlusion, to change or modify the proposed orthodontic prescription for certain ones or for all of the orthodontic objects to achieve a desired functional or aesthetic result. The practitioner may modify the proposed prescription and view the orthodontic objects at the associated determined positions until an acceptable result is achieved. By allowing the practitioner to visualize final occlusion for a proposed prescription, and/or by allowing the practitioner to modify the proposed prescription until an acceptable functional and aesthetic result is achieved, bracket rebonding resulting from inaccurate bracket placement may be reduced and treatment time may be minimized.

As used herein, the terms "orthodontic prescription" or "prescription" refer to the geometric attributes inherent in the selected orthodontic appliances and to relative positions and orientations of each appliance with respect to its associated tooth. Practitioner 8 may interact with the modeling software to view the 3D digital representation of the teeth and to define a proposed orthodontic prescription. Practitioner 8 may define the proposed orthodontic prescription by selecting virtual brackets that embody certain geometric attributes and precisely positioning those virtual brackets on individual teeth within the modeled dental arch. During this process, the modeling software manipulates each bracket as a separate object within the 3D environment, and fixes the position of each bracket within the 3D space relative to a coordinate system associated with the bracket's associated tooth. Consequently, practitioner 8 is able to independently view and precisely locate each bracket within the 3D environment relative to its respective tooth.

Once practitioner 8 defines the proposed orthodontic prescription, client computing device determines positions of the teeth based on the proposed prescription and the practitioner has indicated his or her approval, client computing device 4 communicates the bracket placement positions to manufacturing facility 12 via network 14. In response, manufacturing facility constructs an indirect bonding tray 16 for use in physically placing brackets on the teeth of patient 6. In other words, manufacturing facility 12 fabricates indirect bonding tray 16 based on the bracket placement positions selected by practitioner 8 within the 3D environment presented by client computing device 4. Manufacturing facility 12 may, for example, use conventional commercially available brackets selected by practitioner 8 to form indirect bonding tray 16. Manufacturing facility 12 forwards indirect bonding tray 16 to practitioner 8 for use in a conventional indirect bonding procedure to place the brackets on the teeth of patient 6.

Alternatively, client computing device 4 need not forward the bracket placement positions to manufacturing facility 12. Client computing device 4 may instead output, e.g., display or print, the relevant distances and angles for each bracket to assist practitioner 8 in manually positioning the brackets on the teeth of patient 6.

Although the description will generally discuss the display and positioning of orthodontic brackets, it shall be understood that client computing device 4 may display and/or position any type of orthodontic appliance without departing from the scope of the present invention. Examples of such orthodontic appliances include orthodontic brackets, buccal tubes, sheaths or buttons. In addition, client computing device 4 need not display a full visual representation of the appliance. Rather, a portion of the appliance may be displayed. As another alternative, client computing device 4 need not display the appliance itself. Rather, another object associated with an appliance or with the placement of an appliance may be shown instead of or in addition to the appliance itself. Examples of such other objects include crosshairs (intersecting lines indicating the position on a tooth where the center of an appliance is to be placed), placement jigs, placement guides, or other peripheral which may represent or be attached to an appliance, or which may be otherwise associated with an appliance and/or its placement. The terms "appliance" or "bracket" as used herein shall therefore be understood to include any type of appliance, a full or partial representation of an appliance, or any object associated with an appliance and/or its placement.

Client computing device 4 may show a digital representation of an entire dental arch, a portion of a dental arch, an individual tooth within the dental arch, or a portion of a tooth within the dental arch, or some combination thereof for viewing by the practitioner. Client computing device 4 may also show a digital representation of appliances on all of the teeth in a dental arch, the appliances on a portion of the teeth in a dental arch, an appliance on a single tooth, or an appliance on a portion of a tooth. Similarly, client computing device 4 may show a digital representation of an entire appliance, a portion of an appliance, or simply the crosshairs of an appliance (which may indicate, for example, the location on a tooth where the center of the appliance is to be placed). It shall be understood, therefore, that the image presented to the practitioner 8 by client computing device 4 may take many different forms, and that the invention is not limited in this respect.

The 3D representation of the dental arch may be initially generated by digitally scanning a physical dental impression of the teeth of patient 6 or by scanning a casting made from the impression. Alternatively, practitioner 8 may use an intraoral scanner to produce the 3D digital representation directly from the teeth of patient 6. Other methods of scanning may also be used.

Figure 2:
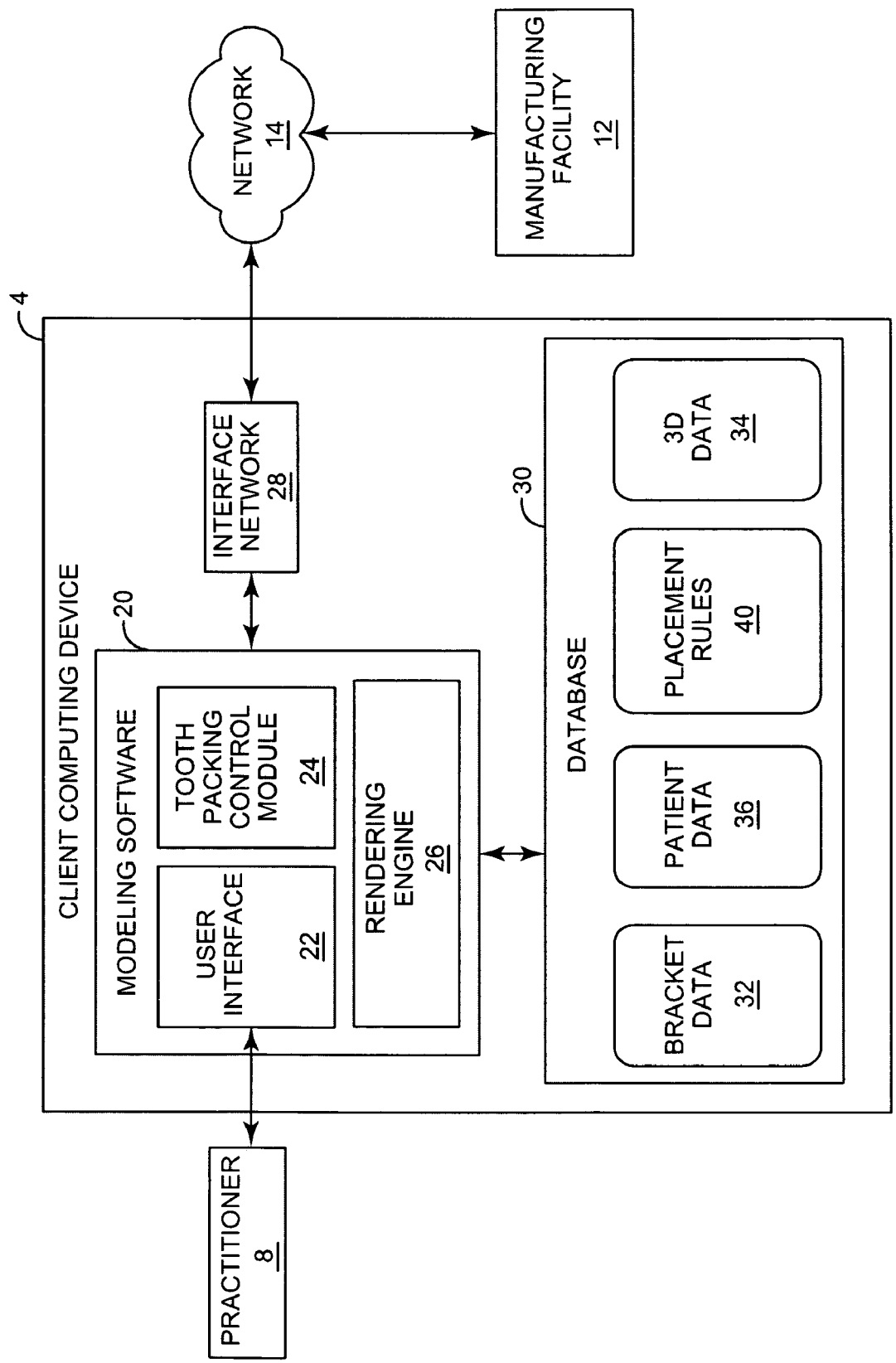
FIG. 2 is a block diagram illustrating an example embodiment of the client computing device of FIG. 1 in further detail.

FIG. 2 is a block diagram illustrating an example embodiment of client computing device 4 in further detail. In the illustrated embodiment, client computing device 4 provides an operating environment for modeling software 20. As described above, modeling software 20 presents a modeling environment for modeling and depicting the 3D representation of the teeth of patient 6 (FIG. 1). In the illustrated embodiment, modeling software 20 includes a user interface 22, a tooth packing control module 24 and a rendering engine 26.

User interface 22 provides a graphical user interface (GUI) that visually displays the 3D representation of the patient's teeth as well as 3D representations of the brackets. In addition, user interface 22 provides an interface for receiving input from practitioner 8, e.g., via a keyboard and a pointing device, for manipulating the brackets and placing the brackets on respective teeth within the modeled dental arch. User interface 22 also visually displays a 3D representation of the final occlusion generated by tooth packing control module 24.

Modeling software 20 interacts with database 30 to access a variety of data, such as bracket data 32, 3D data 34, patient data 36, and placement rules 40. Database 30 may be represented in a variety of forms including data storage files, lookup tables, or a database management system (DBMS) executing on one or more database servers. The database management system may be a relational (RDBMS), hierarchical (HDBMS), multi-dimensional (MDBMS), object oriented (ODBMS or OODBMS), object relational (OR-DBMS) or other type of database management system. The data may, for example, be stored within a single relational database such as SQL Server from Microsoft Corporation. Although illustrated as local to client computer device 4, database 30 may be located remote from the client computing device and coupled to the client computing device via a public or private network, e.g., network 14.

Bracket data 32 describes a set of commercially available brackets that may be selected by practitioner 8 and positioned within the 3D modeling environment. For example, bracket data 32 may store a variety of attributes for the commercially available brackets, such as dimensions, slot locations and characteristics, torque angles, angulations and other attributes. User interface 22 provides a menu-driven interface by which practitioner 8 selects the type of brackets for use in defining an orthodontic prescription for patient 6.

Patient data 36 describes a set of one or more patients, e.g., patient 6, associated with practitioner 8. For example, patient data 36 specifies general information, such as a name, birth date, and a dental history, for each patient. In addition, patient data 36 specifies a current prescription specified for each of the patients, including the types of brackets selected by practitioner 8 for use with each of the patients, and their associated positions and orientations on the teeth of patient 6.

The orthodontic industry has developed standard prescriptions for many commercially available orthodontic brackets. These standardized prescriptions generally tend to satisfy the functional and the aesthetic requirements for most patients. The standardized prescriptions may be used to achieve uniformity among patients or to avoid the more time consuming process of devising a custom set of metrics for each individual patient.

For some patients, a standardized set of metrics for the teeth in the dentition may be satisfactory. For other patients, practitioner 8 may desire to create a customized prescription to achieve a more aesthetically pleasing result, or to more adequately take into account that patient's malocclusions. As another example, a combination of standardized and customized prescriptions for different teeth in the dentition may be used. Practitioner 8 inputs the desired prescription via user interface 22, which is then stored in database 30 as patient data 36.

Placement rules 40 may specify industry-defined placement rules for commercially available brackets. In addition, placement rules 40 may include user-defined rules specified by practitioner 8 or other rules for controlling bracket placement. For example, one rule for certain commercially available brackets is to align the medial line or longitudinal axis of the bracket with the Facial Axis of the Clinical Crown (FACC) of the tooth. The FACC is defined as the curved line formed by the intersection of the mid-sagittal plane and the facial surface of the tooth. Another exemplary industry-defined placement rule is to place the center of a base of the bracket on the FACC of the tooth equidistant from the occlusal edge or occlusal-most point on the FACC and the gingival margin of the crown. This location is also known as the Facial Axis Point (FA Point). As another example, practitioner 8 may desire to place brackets at a position that is different from the FA Point. Consequently, practitioner 8 may specify different prescriptions for different types of teeth in the dentition, for different types of brackets, or both. Optionally, the prescription may be based in whole or in part on known rules associated with a particular type of the appliances selected by practitioner 8.

Rendering engine 26 accesses and renders 3D data 34 to generate the 3D view presented to practitioner 8 by user interface 22. More specifically, 3D data 34 includes information defining the 3D objects that represent each tooth and bracket within the 3D environment. Rendering engine 26 processes each object to render a 3D triangular mesh based on viewing perspective of practitioner 8 within the 3D environment. User interface 22 displays the rendered 3D triangular mesh to practitioner 8, and allows the practitioner to change viewing perspectives and manipulate objects within the 3D environment.

Tooth packing control module 24 receives a proposed prescription from patient data 36 and automatically places teeth along an archwire based on the proposed prescription. The digital representation of the resulting final occlusion may be displayed on user interface 22. Practitioner 8 may then view the visual representation of the final occlusion to determine whether the proposed prescription will give a desired functional and/or aesthetic result or whether the proposed prescription should be modified.

Orthodontic appliances, or brackets as they will generally be referred to herein, may initially be placed in the 3D environment using any of several different methods. For example, the brackets may initially be placed in the 3D environment using the method described in copending and commonly assigned U.S. patent application Ser. No. 10/734,323, entitled "Method of Placing Orthodontic Brackets on Teeth in a 3D Virtual World", filed Dec. 12, 2003 to Raby, et al., which is incorporated herein by reference in its entirety. Manual adjustment of orthodontic brackets may be assisted by use of visual planar guides, as described in copending and commonly assigned U.S. patent application Ser. No. 10/771,641, entitled "Planar Guides to Visually Aid Orthodontic Appliance Placement within a Three-Dimensional (3D) Environment", filed Feb. 4, 2004 to Raby, et al., which is incorporated herein by reference in its entirety. In that application, a system visually aids the user in manual placement of brackets through manual adjustments to bracket position and orientation. Other methods of placing or adjusting the position of brackets on the teeth may also be used. For example, a system for automatic adjustment of an orthodontic appliance to a desired occlusal height is described in copending and commonly assigned U.S. patent application Ser. No. 10/903,686, entitled "AUTOMATIC ADJUSTMENT OF AN ORTHODONTIC BRACKET TO A DESIRED OCCLUSAL HEIGHT WITHIN A THREE-DIMENSIONAL (3D) ENVIRONMENT", filed Jul. 30, 2004 to Raby, et al., which is incorporated herein by reference in its entirety. A system for moving teeth and/or brackets along an archwire is described in copending and commonly assigned U.S. patent application Ser. No. 10/959,625 entitled, "Movement of Orthodontic Objects Along a Virtual Archwire within a Three-Dimensional Environment", 3M filed on even date herewith to Raby, et al. which is incorporated herein by reference in its entirety.

It shall be understood that these and/or any other techniques may be used to initially place the orthodontic appliances on the teeth in the 3D environment and thus determine the patient's prescription, and that the invention is not limited in this respect. To automatically determine positions of teeth associated with a proposed prescription, tooth packing control module 24 "packs" (in other words, places or positions) the teeth along a virtual archwire. In particular, tooth packing control module 24 automatically determines the positions of the teeth along the archwire so that adjacent teeth do not overlap and are no more than a defined distance apart.

Once tooth packing control module 24 has determined the tooth positions, rendering engine 26 generates a representation of the relative position and orientation of each virtual bracket with respect to the virtual arch at the conclusion of treatment. In one embodiment, tooth packing control module 24 automatically determines the positions of teeth along the archwire based on the proposed prescription using the straight-wire concept. However, it shall be understood that methods other than the straight wire concept could also be used, and that the invention is not limited in this respect. The virtual representation of the teeth at the determined positions approximates the actual relative positions and orientations of the patient's teeth at the conclusion of treatment.

In general, tooth packing control module 24 initially places a tooth distance d along the archwire from the previous tooth placed in that quadrant. If the tooth is the first tooth to be placed in a quadrant, tooth packing control module 24 initially places the tooth a distance d along the archwire from the midline of the archwire. Tooth packing control module 24 moves the teeth in decreasing amounts, for example, half of the previous movement, until a desired tolerance t is reached. In one embodiment, the tooth's first movement may be d/2 units, the second will be d/4, and so on. After each movement j, the tooth is within $d/2^j$ units of its ideal (touching the adjacent tooth at one point of contact) position ($t=d/2^j$).

Figure 3A:
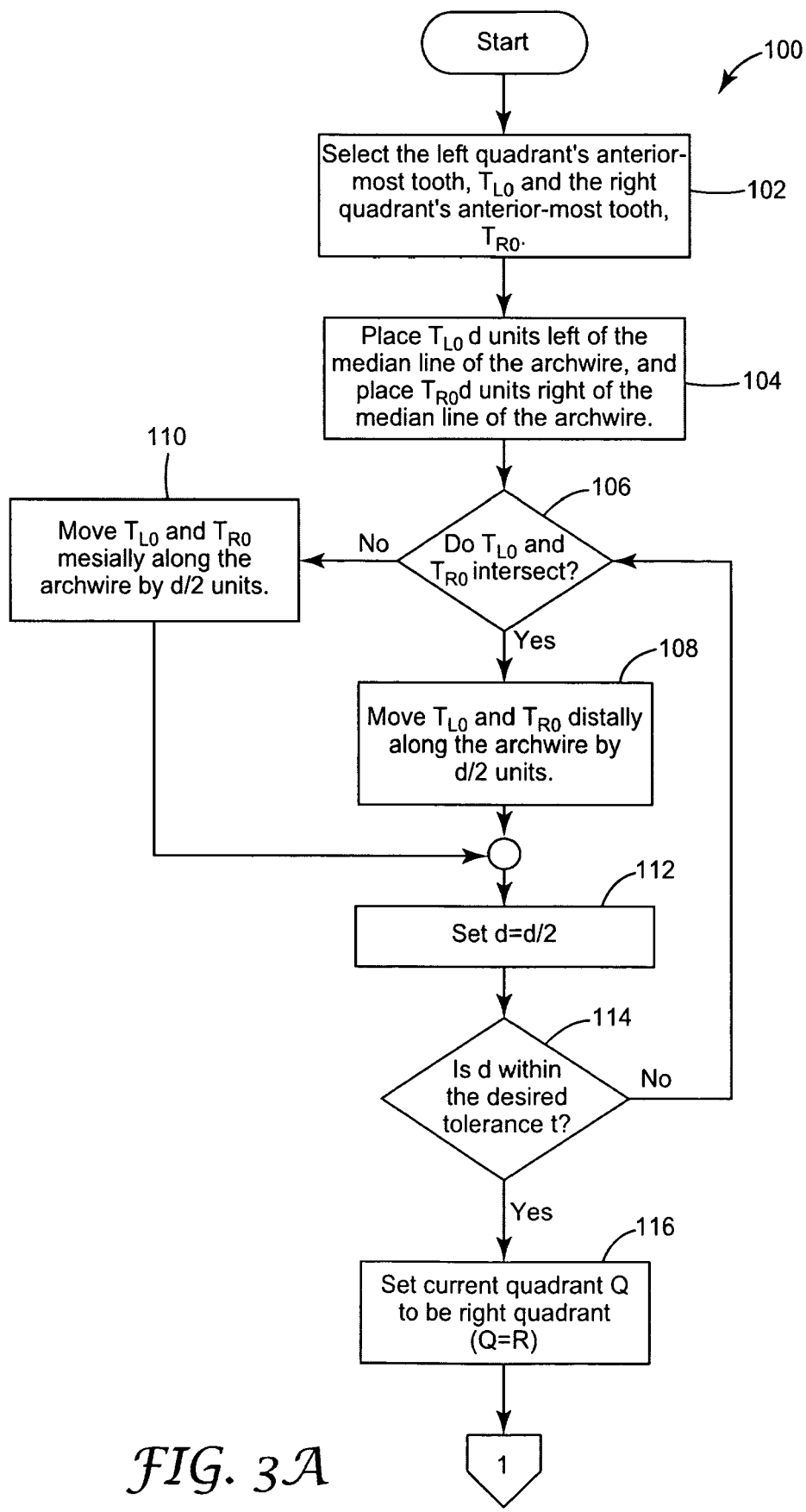
FIGS. 3A and 3B are a flowchart illustrating exemplary operation of modeling software executing on the client computing device to place orthodontic objects along an archwire.
Figure 3B:
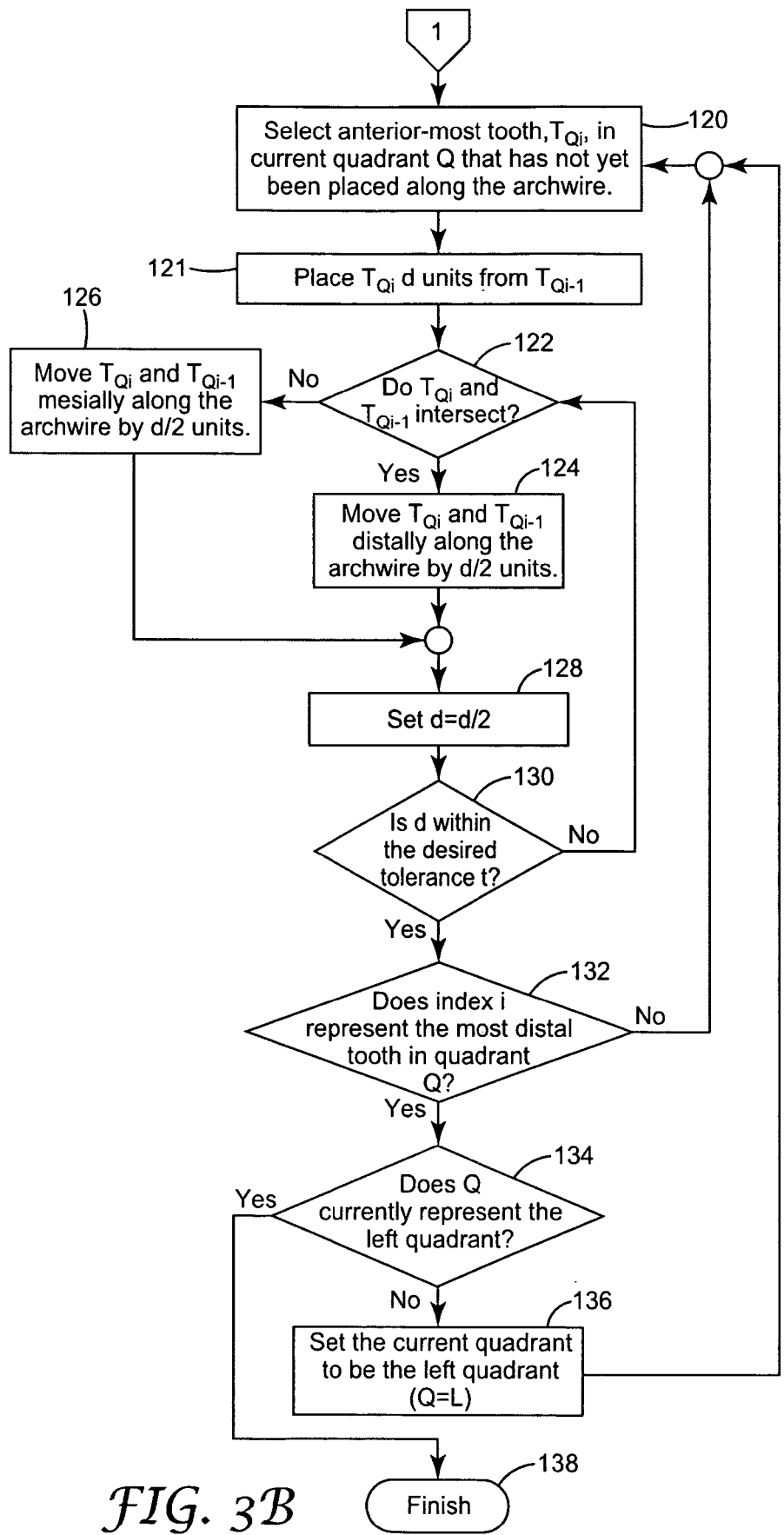

FIGS. 3A and 3B are a flowchart 100 illustrating a method of automatically determining positions of teeth along an archwire based on a proposed orthodontic prescription. More specifically, the flowchart of FIGS. 3A and 3B illustrates operation of modeling software 20 in automatically determining positions of teeth along a virtual archwire to generate a digital representation of a final occlusion within the 3D virtual environment based on the proposed orthodontic prescription.

In a given arch, tooth packing control module 24 first identifies the anterior-most tooth in each of the right and left quadrants, $T_{R0}$ and $T_{L0}$, (102). Initially, tooth packing control module 24 places each tooth along the archwire a defined distance d from the median of the archwire (104). Tooth packing control module 24 places a tooth along the archwire, orienting the tooth such that the archwire passes through the slot of the bracket on that tooth. Tooth packing control module 24 next determines whether the two teeth intersect (106). One exemplary method by which tooth packing control module 24 may determine whether two teeth intersect is described below with respect to FIGS. 12A and 12B. If the two teeth intersect, tooth packing control module 24 moves each tooth away (distally) from the median line of the arch wire by d/2 units (108). If they do not intersect, tooth packing control module 24 moves each tooth toward (mesially) the median line by d/2 units (110). The distance d is set to d/2 for the next iteration (112). Each iteration, tooth packing control module 24 moves both teeth either toward the median line of the archwire if they do not intersect or moves them away from the median line of the archwire if they do intersect. Tooth packing control module 24 continues this process, setting the distance d to one half of its previous value (112) each iteration, until the distance d is within a desired tolerance t (114). The tolerance t may be a defined value or may be a defined number of iterations.

After placing the anterior-most tooth in each of the left and right quadrants within a desired tolerance t along the archwire, tooth packing control module 24 places the remaining teeth in that arch. In one embodiment, tooth packing control module 24 places the teeth along the archwire one quadrant at a time. For example, tooth packing control module 24 may begin with the right quadrant (116). Tooth packing control module 24 may then place the second anterior-most tooth of that quadrant ($T_{Qi}$) distance d along the archwire distally from the final position of the anterior-most tooth ($T_{Qi-1}$) of that quadrant (120) as determined in the previous step. An index i denotes the selected tooth in the current quadrant (denoted by Q) and ranges from 0 to 1 less than the number of teeth within the quadrant. As with placement of the anterior-most teeth, tooth packing control module 24 then determines whether the anterior-most tooth and the second anterior-most tooth intersect (122).

If the teeth intersect, tooth packing control module 24 moves the second anterior-most tooth away from the anterior-most tooth by one half the starting distance, d/2 (124). If they do not intersect, tooth packing control module 24 moves the second anterior-most tooth toward the anterior-most tooth by half the starting distance, d/2 (126). In preparation for the next iteration, tooth packing control module 24 sets the distance d to d/2 (128).

Tooth packing control module 24 continues in this manner until the second anterior-most tooth is placed within a desired tolerance t (130). Tooth packing control module 24 checks the value of index i to determine whether the distal-most tooth in that quadrant has been placed (132). If not, tooth packing control module 24 repeats this process, iteratively placing each of the remaining teeth in the right quadrant, each iteration placing the next remaining anterior-most tooth in that quadrant. Tooth packing control module 24 then checks whether the teeth in both quadrants have been placed by determining whether it has placed teeth in the last remaining quadrant (134). If not, tooth packing control module 24 then repeats the entire process with the remaining quadrant (the left quadrant, in this example) (136). After tooth packing control module 24 places all of the teeth in the left quadrant (134), adjacent teeth along the entire arch are positioned along the archwire, without intersecting, within some specified and predetermined tolerance t.

Figure 4:
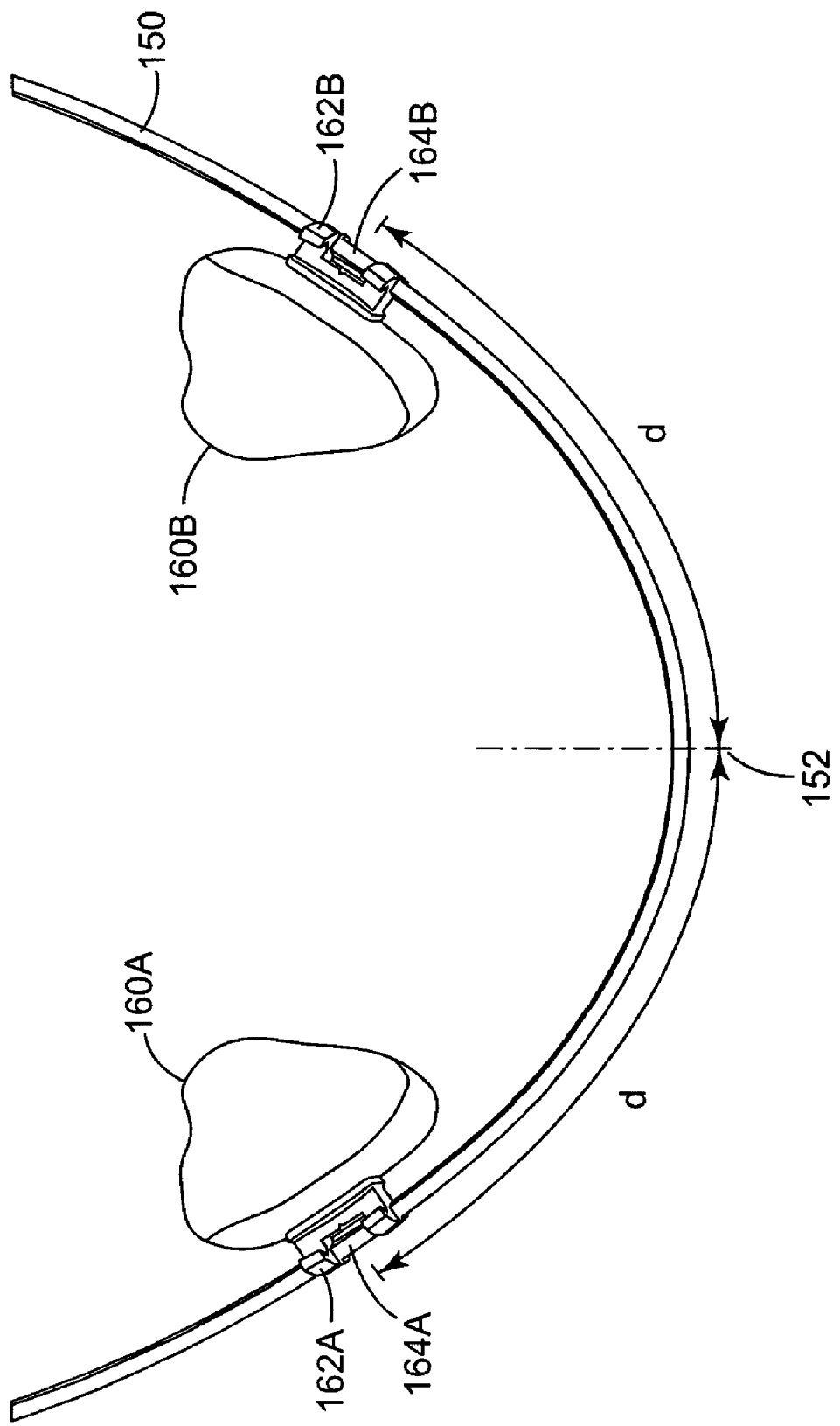
FIGS. 4-8 illustrate example operation of the tooth packing control module placing orthodontic objects along an archwire.
Figure 5:
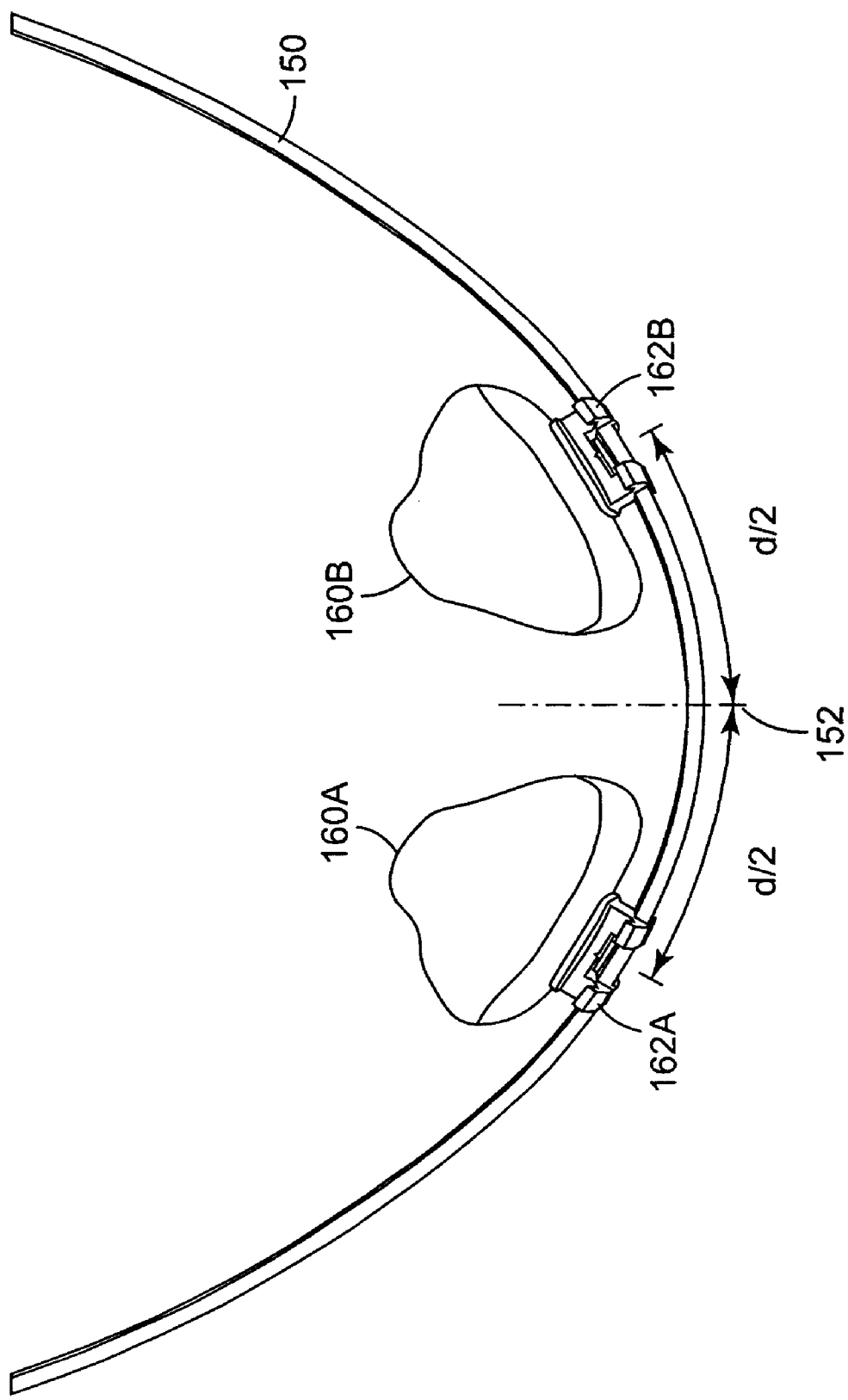

FIGS. 4-8 illustrate determining positions of the teeth along an archwire according to the method described above. FIG. 4 shows the two anterior-most teeth 160A and 160B each placed distance d from the midline 152 of archwire 150. The distance d may be measured from any appropriate point on the tooth, such as the midpoint of an appliance associated with the tooth, e.g., the bracket. Each tooth 160A and 160B is oriented such that archwire 150 passes through each of the respective slots 164A and 164B of brackets 162A and 162B. Tooth packing control module 24 performs an intersection check and determines that teeth 160A and 160B do not in intersect. Tooth packing control module 24 then moves each tooth 160A and 160B a distance of d/2 mesially along archwire 150 (i.e., toward archwire midline 152). FIG. 5 shows anterior-most teeth 160A and 160B after tooth packing control module 24 moves them both a distance of d/2 mesially toward the midline 152 of archwire 150.

Figure 6:
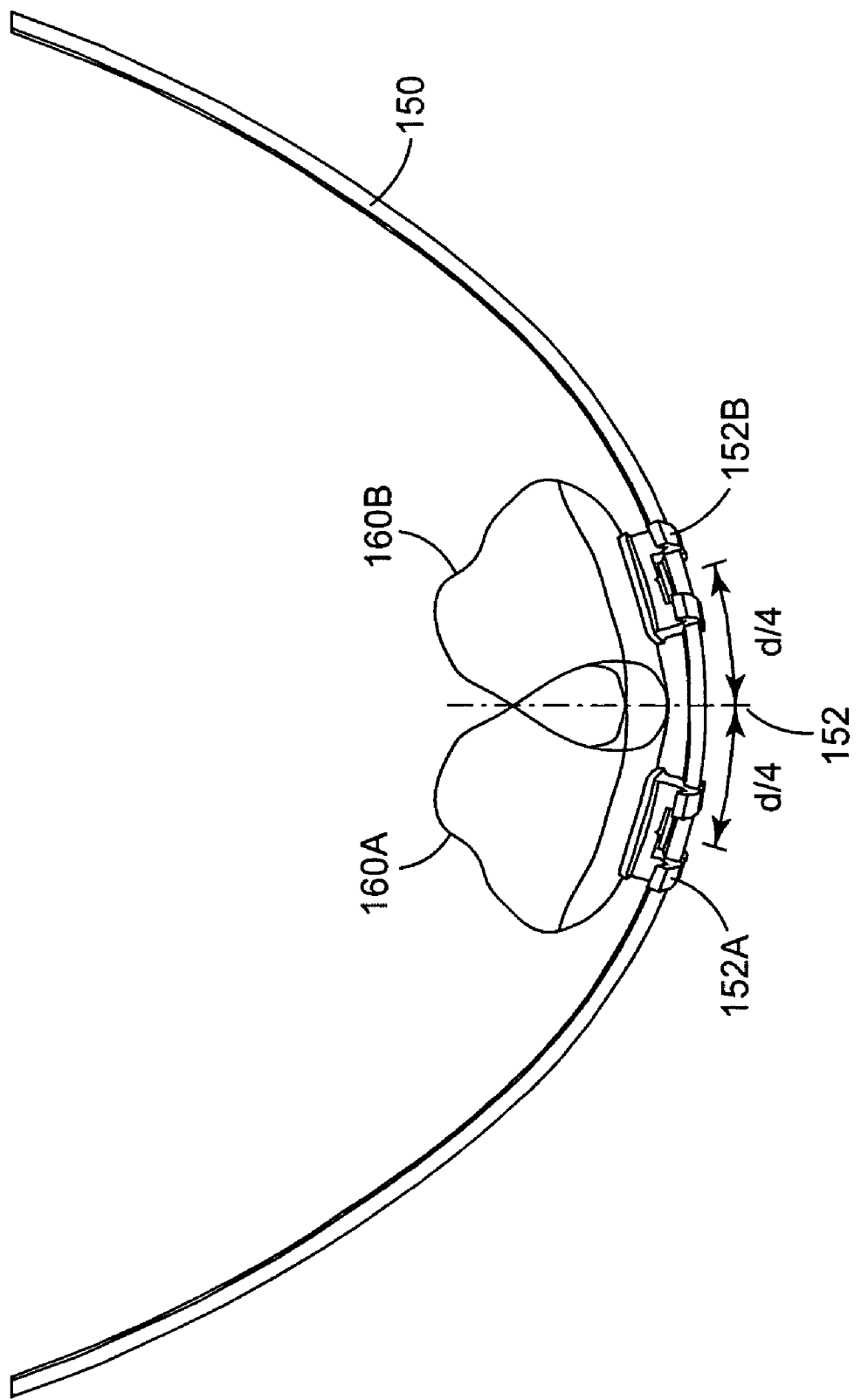

Tooth packing control module 24 next performs an intersection check at this new position and determines that, in this example, teeth 160A and 160B do not intersect. Therefore, tooth packing control module 24 moves each tooth 160A and 160B a distance of d/4 mesially along archwire 150 (i.e., toward archwire midline 152). FIG. 6 shows anterior-most teeth 160A and 160B after another iteration, i.e., after tooth packing control module 24 moves both teeth 160A and 160B a distance of d/4 toward the midline 152 from their previous position shown in FIG. 5.

Figure 7:
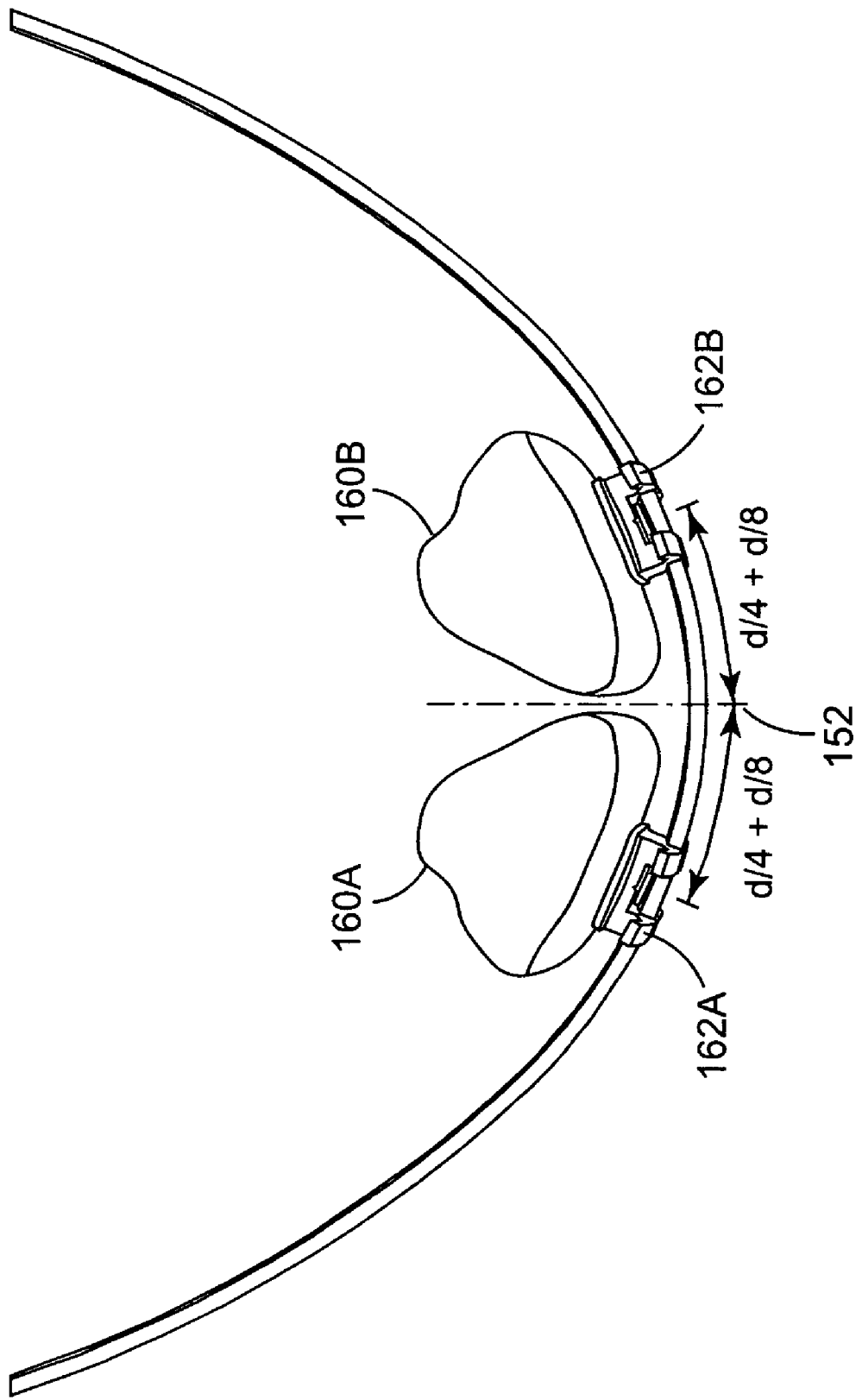

Tooth packing control module 24 performs an intersection check at this new position shown in FIG. 6 and determines that the teeth are in intersection. Consequently, tooth packing control module 24 moves each tooth 160A and 160B a distance of d/8 distally along archwire 150 away from midline 152 as shown in FIG. 7. After this movement, the teeth 160A and 160B in FIG. 7 no longer intersect.

Tooth packing control module 24 continues this process until all of the teeth in the current quadrant are placed within some desired predetermined tolerance t. After each movement j, t is equal to $d/2^j$, and this tolerance represents the maximum distance that each tooth lies from its ideal position (defined as touching the adjacent tooth at one point of contact).

Figure 8:
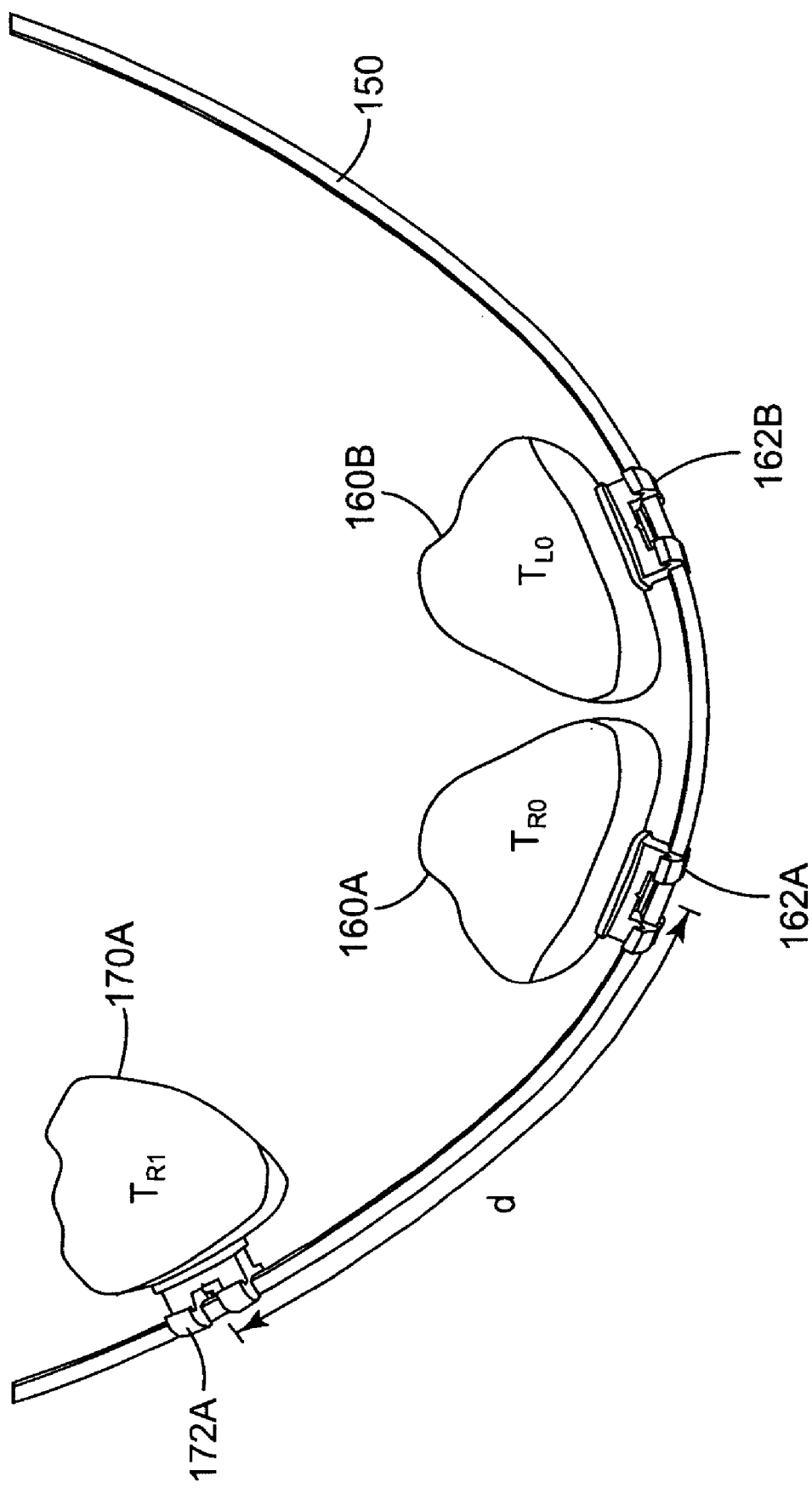

When teeth 160A and 160B are within desired tolerance t, tooth packing control module 24 may place the second-most anterior tooth in the right quadrant along archwire 150. FIG. 8 shows second-most anterior tooth 170A whose bracket 172A is placed a distance d from the bracket 162A of anterior-most tooth 160A. Tooth packing control module 24 repeats this process for the second-most anterior tooth 170A in the right quadrant until that tooth is within the desired tolerance t of the anterior-most tooth. Tooth packing control module 24 repeats this entire process until all teeth in the right quadrant have been placed, and then again until all teeth in the left quadrant have been placed. The same types of movements shown above are performed for the subsequent teeth, except that any teeth already placed do not move.

Figure 9A:
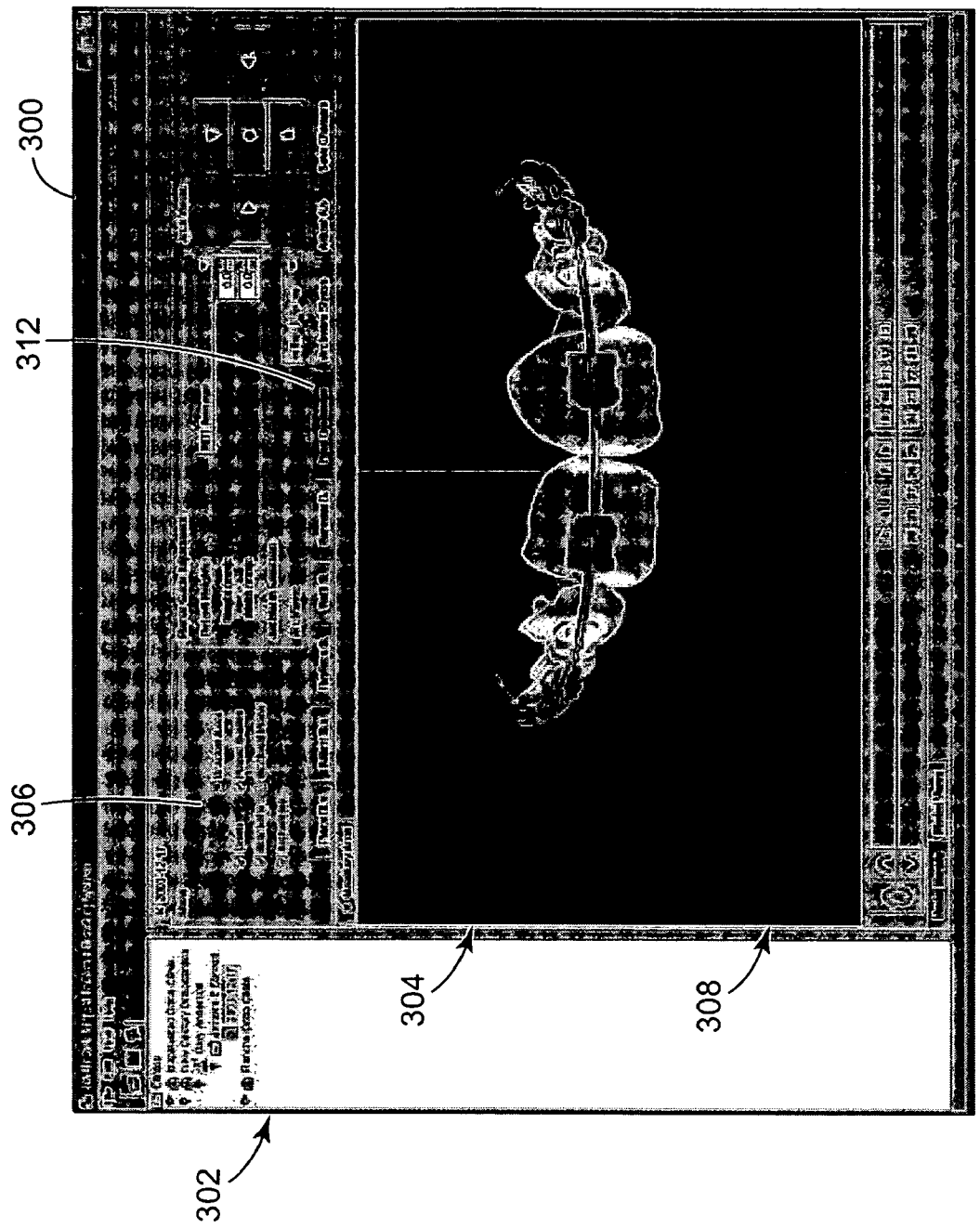
FIGS. 9A and 9B are display diagrams of an exemplary user interface presented by the modeling software.
Figure 9B:
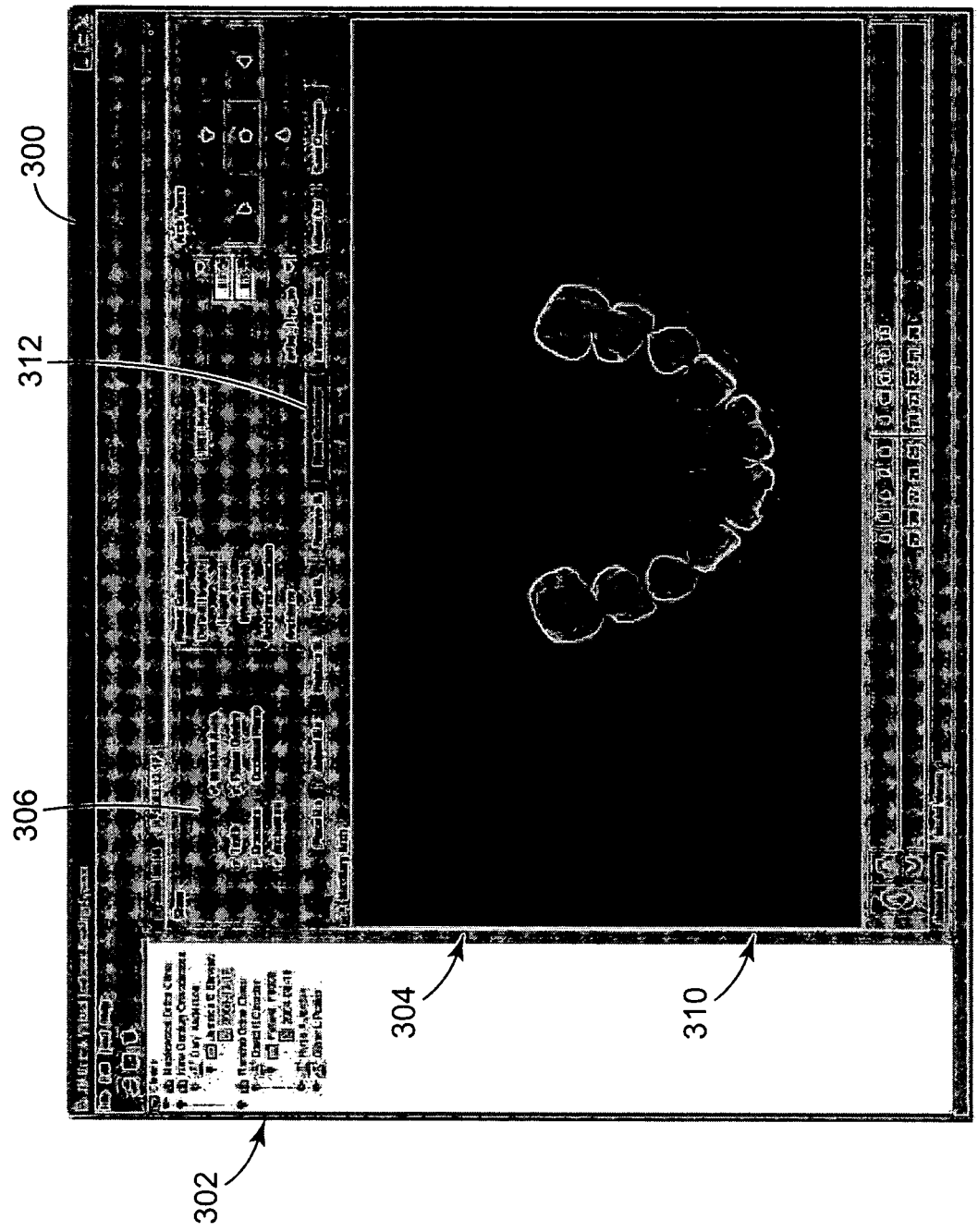

FIGS. 9A and 9B are display diagrams illustrating an exemplary graphical user interface (GUI) presented by modeling software 20. For example, FIGS. 9A and 9B illustrate an exemplary user interface 300 that depicts the teeth in accordance with the positions determined by tooth packing control module 24.

In the illustrated embodiment of FIG. 9A, user interface 300 includes a menu input area 302 by which a user, e.g., practitioner 8, accesses a proposed electronic prescription for patient 6. User interface 300 further includes display area 304 for presenting the 3D rendered representation of the teeth of patient 6. In the example of FIG. 9A, display area 304 presents a virtualized facial view 308 of the dental arch of patient 6 resulting from a proposed orthodontic prescription. In the example of FIG. 9B, display area 304 presents a virtualized bottom view 310 of the dental arch of patient 6 with the teeth in the positions determined by tooth packing control module 24 based on the proposed orthodontic prescription. User interface 300 provides selection mechanism 306 by which practitioner 8 can selectively enable and disable the rendering and display of any of several different views of the patient's dental arch within the display area 302. The 3D rendered representations 308 and 310 of the final occlusion allow practitioner 8 to determine whether the proposed prescription will satisfactorily achieve functional occlusion and meet the practitioner's and/or the patient's aesthetic requirements.

FIGS. 10A, 10B, 11A and 11B illustrate a simplified example of a method that modeling software 20 may utilize to determine whether two teeth intersect. In one embodiment, the method makes use of the fact that each tooth includes a bracket whose slot fits around the archwire, a planar object. After initial placement of the bracket on the tooth, modeling software 20 stores a 3D Affine transform in database 30. This transform includes details about the position and orientation of each bracket in relation to its associated tooth. Modeling software 20 may also generate another 3D Affine transform that transforms the original bracket coordinate system to a coordinate system lying in the slot of the bracket and oriented in such a way that the modeling software may extract information about the plane of the bracket's archwire slot. Using these transforms and their associated data, modeling software 20 may define the plane of the archwire in relation to the tooth. This plane intersects the tooth, and the intersection creates a cross-section of the tooth, more specifically a polyline that outlines the cross-section. Multiple tooth cross-sections can be created by considering new planes that lie parallel to the original plane of the archwire and are translated above or below the original plane by some given distance, constrained by the extent of the tooth in those directions.

Figure 10B:
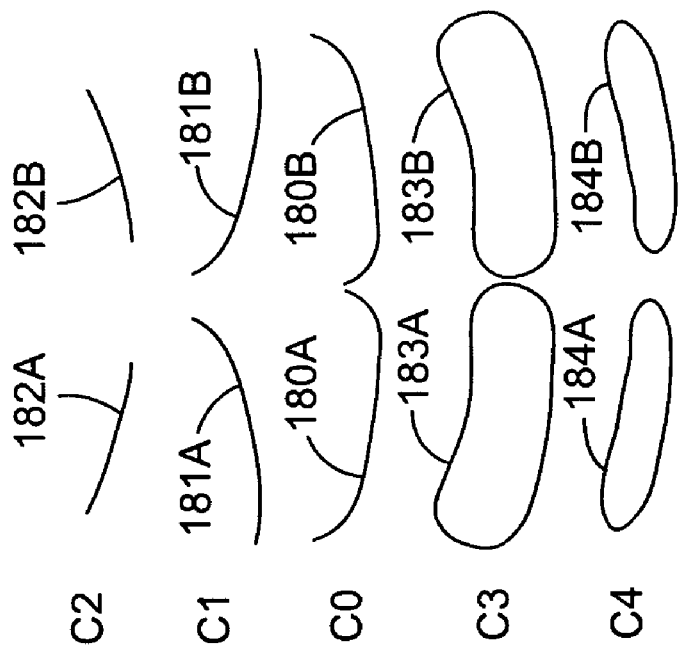
FIGS. 10A, 10B, 11A and 11B show example representations of how the tooth packing control module may determine whether two adjacent orthodontic objects intersect.
Figure 10A:
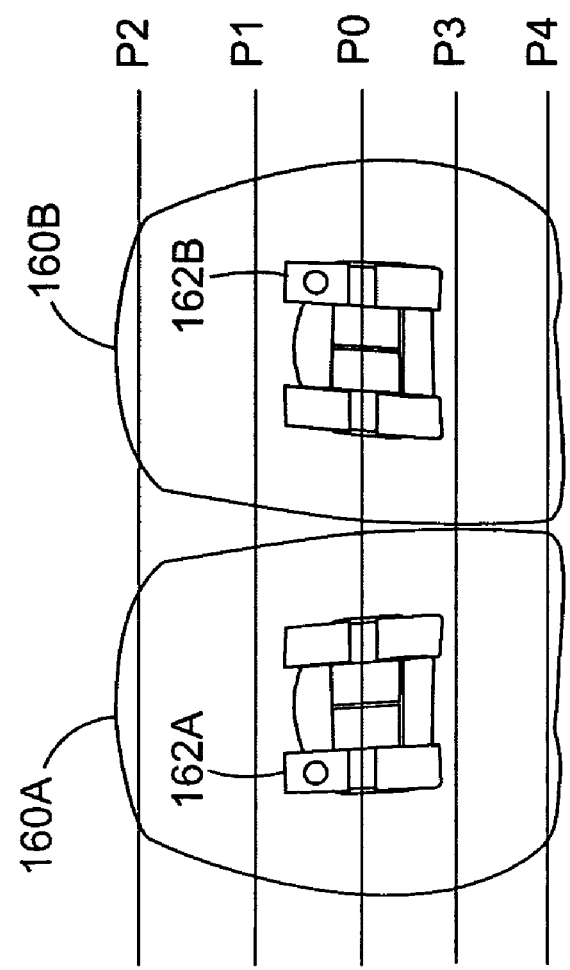

FIG. 10A is an exemplary facial diagram of two anterior-most teeth 160A and 160B and their associated brackets 162A and 162B, respectively. Plane P0 is the plane that lies in the plane of the archwire. Planes P1 and P2 are parallel to plane P0 and lie above plane P0. Planes P3 and P4 are parallel to plane P0 and lie below plane P0. In the example of FIG. 10A, there are two planes drawn above and below the archwire plane. FIG. 10B shows cross-sections C0, C1, C2, C3 and C4 formed by intersections of the corresponding planes P0, P1, P2, P3 and P4, respectively with the teeth 160A and 160B. In FIGS. 10A and 10B, because no intersection is detected in any of the cross-sections, tooth packing control module 24 would determine that teeth 160A and 160B do not intersect.

Figure 11B:
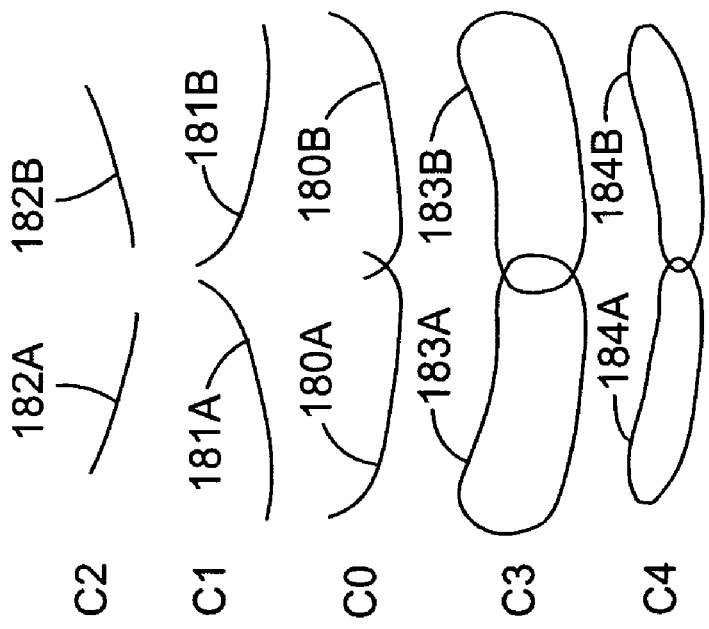
Figure 11A:
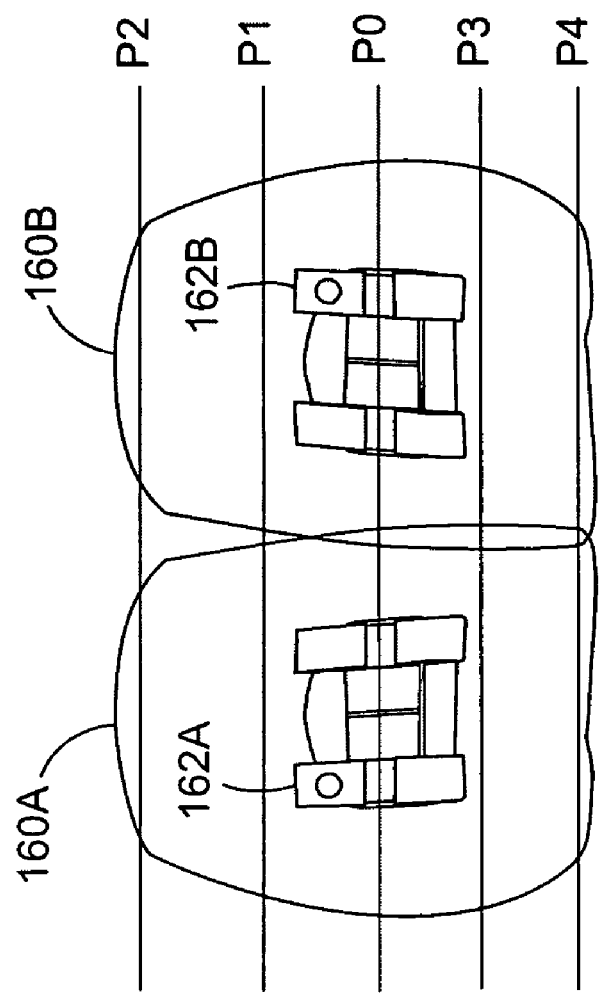

FIG. 11A is a facial diagram of two anterior-most teeth 160A and 160B, their associated brackets 162A and 162B, respectively, and planes P0-P4. FIG. 11B shows corresponding cross-sections C0-C4. In FIGS. 11A and 11B, tooth packing control module 24 would detect intersection in three of the cross-sections (C0, C3, and C4). In this case, tooth packing control module 24 would therefore determine that teeth 160A and 160B in FIGS. 11A and 11B are in intersection.

In practice, tooth packing control module 24 may make use of fewer or many more planes to gather more cross-section and/or polyline information. Use of more cross-sections may increase the accuracy of intersection detection. In one embodiment, at least 50 cross-sections may be used. In another embodiment, at least 100 cross-sections may be used.

It shall be understood, therefore, that one parameter which may be adjusted is the number of planes that are used, thus determining how many cross-sections for each tooth are considered. When more cross-sections are used, the accuracy of the algorithm may be improved. However, when fewer cross-sections are used, the execution speed of the algorithm may be improved. It shall be understood that although specific examples are given herein, the precise number of planes and cross-sections used may be varied to achieve the desired levels of speed and accuracy, and that the invention is not limited in this respect.

Tooth packing control module 24 determines the set of planes used to find cross-sections in each of the two teeth that are being tested for intersection. Because tooth packing control module 24 uses the same plane to obtain a cross-section from each tooth, the cross-sections lie in the same plane and can be tested for intersection. If one or more corresponding cross-sections intersect, then tooth packing control module 24 determines that the two tooth objects intersect.

In general, tooth packing control module 24 tests each segment of a polyline for one tooth for intersection with each segment of a polyline for the second tooth. If any polyline segment from the first tooth intersects any polyline segment of the second tooth, tooth packing control module 24 determines that the two teeth intersect. If none of the corresponding polyline segments intersect, then tooth packing control module 24 determines that the two teeth are not in intersection.

Figure 12A:
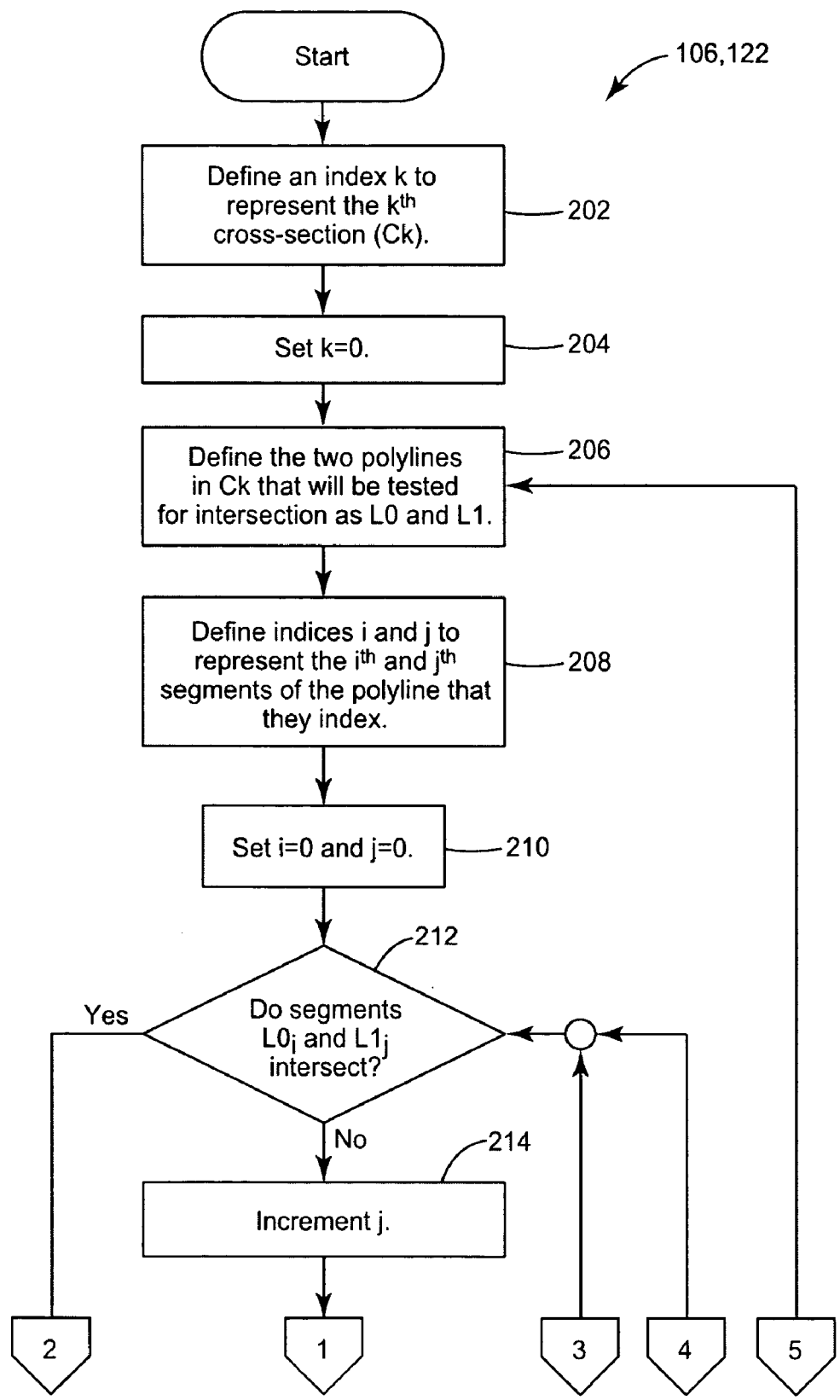
FIGS. 12A and 12B are a flowchart illustrating exemplary operation of modeling software executing on the client computing device to determine whether two adjacent orthodontic objects intersect.
Figure 12B:
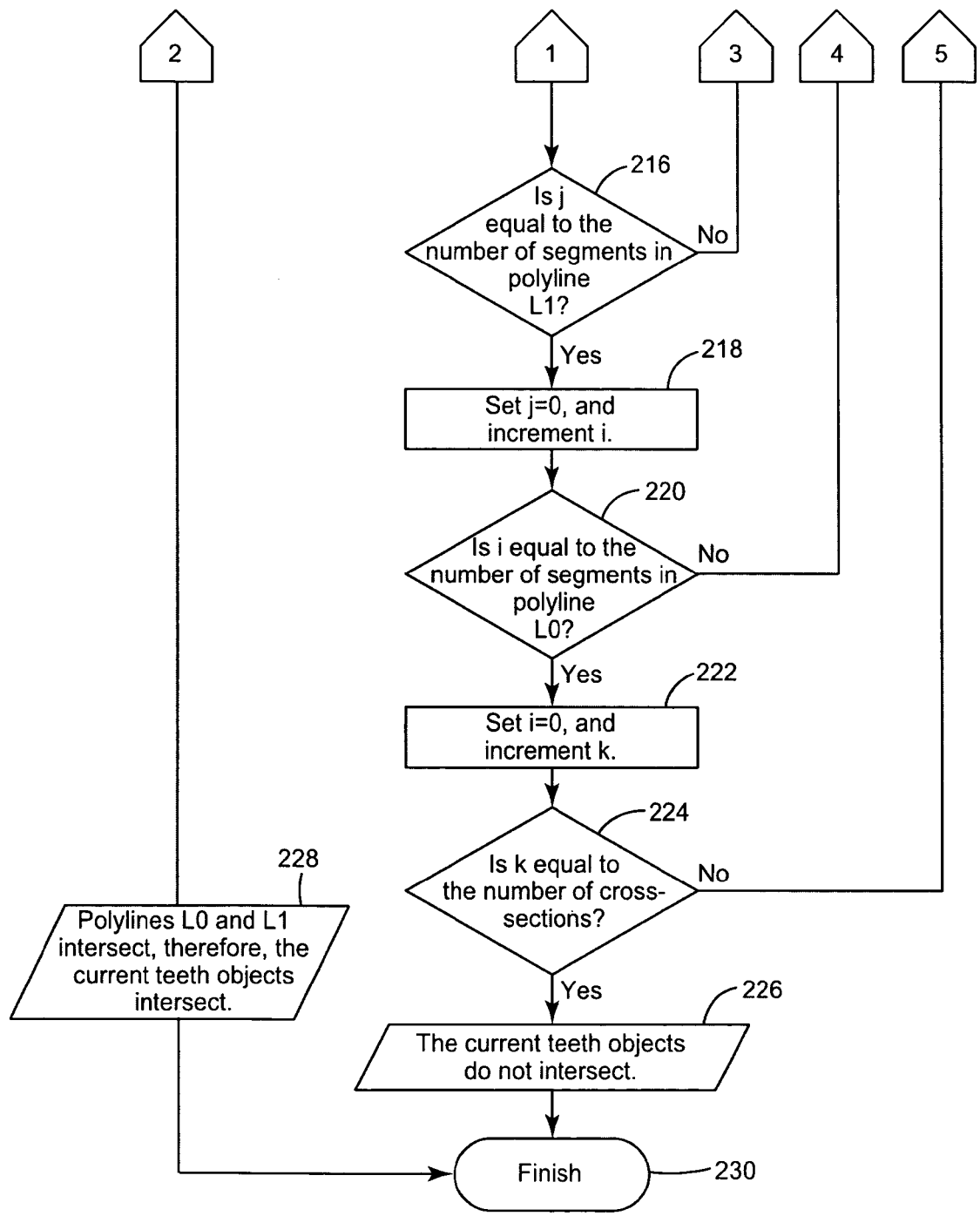

FIGS. 12A and 12B are a flowchart illustrating one example process that modeling software 20 may utilize to determine whether two teeth objects intersect based on a set of cross-sections like those described above. This method may, for example, be used in the flowchart of FIGS. 3A and 3B at reference numeral 106 and again at reference numeral 122.

In general, the method shown in FIGS. 12A and 12B tests each cross-section for intersection between the two teeth. To do this, tooth packing control module 24 chooses a first segment on a first one of the teeth and tests that first segment for intersection with all of the segments on the second tooth. Then tooth packing control module 24 chooses a second segment on the first tooth and tests that second segment for intersection with all of the segments on the second tooth, and so on until all of the segments in the current polyline on the first tooth have been tested for intersection with all of the segments in the current polyline on the second tooth. The process continues until all cross-sections for the two teeth have been tested for intersection. If any of the segments are found to intersect, tooth packing control module 24 determines that the two teeth intersect. If none of the segments in any of the polylines are found to intersect, tooth packing control module 24 determines that the two teeth do not intersect.

In FIGS. 12A and 12B, tooth packing control module 24 first defines an index k (202). Index k represents the current cross-section ($C_k$), and is set to zero (204) on the first iteration of the process. Tooth packing control module 24 next defines two polylines L0 and L1 in cross-section $C_k$ that will be tested for intersection. L0 represents the polyline on a first one of the teeth being checked for intersection. For example, L0 may represent polyline 180A of cross-section C0 in FIG. 10B or 11B. Similarly, L1 represents the polyline on the second, adjacent tooth being checked for intersection. For example, L1 may represent polyline 180B of cross-section C0 in FIG. 10B or 11B. Table 1 illustrates one example of how cross-sections $C_k$ and polylines L0 and L1 may correspond.

TABLE 1

| $C_k$ | L0 | L1 |
| --- | --- | --- |
| C0 | 180A | 180B |
| C1 | 181A | 181B |
| C2 | 182A | 182B |
| C3 | 183A | 183B |
| C4 | 184A | 184B |

To determine whether the polylines L0 and L1 intersect, tooth packing control module 24 breaks each polyline L0 and L1 into smaller segments. Each segment in polyline L0 is checked for intersection with each segment in polyline L1. In one embodiment, tooth packing control module 24 accomplishes this segment comparison by defining two indices, i and j (206). Index i represents the $i^{th}$ segment of polyline L0, and index j represents the $j^{th}$ segment of polyline L1.

Figure 13:
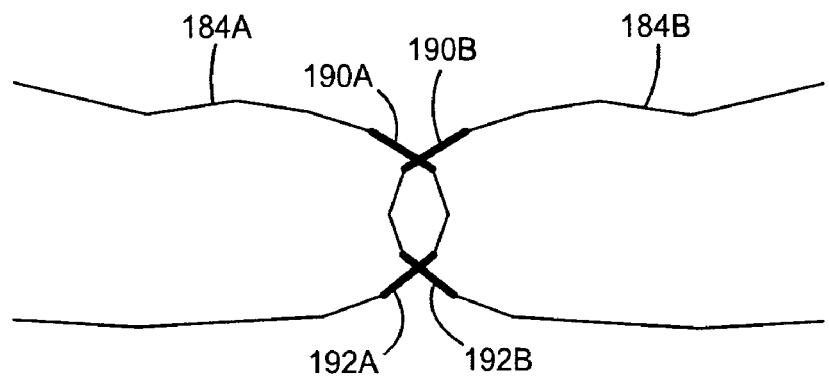
FIGS. 13, 14 and 15 show enlarged illustrations of polyline segments of two adjacent teeth which tooth packing control module may use to determine whether the two orthodontic objects intersect.
Figure 14:
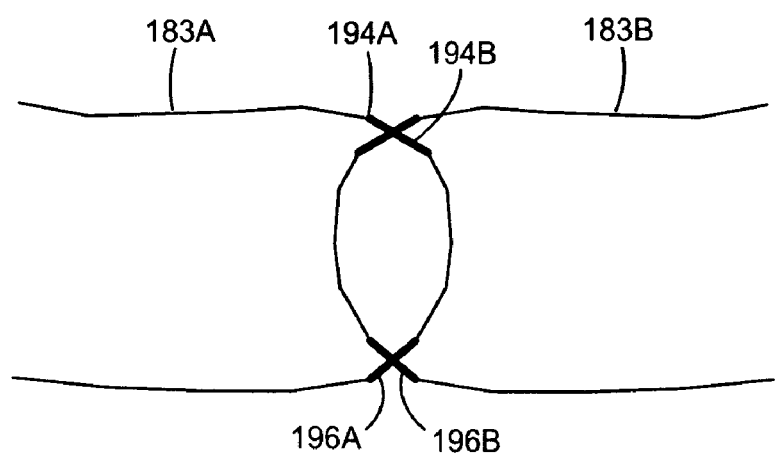
Figure 15:
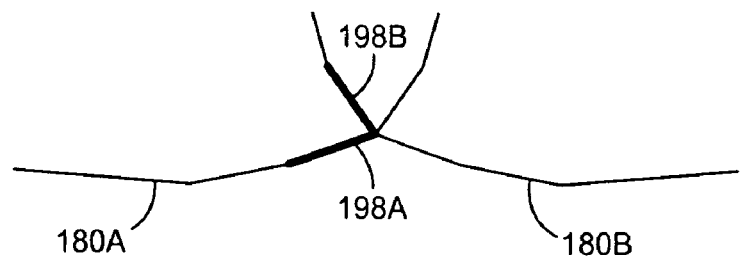

Examples of intersecting segments are shown in FIGS. 13, 14 and 15. FIG. 13 shows an enlarged illustration of cross-section C4 (see FIG. 11B), polyline L0 184A, polyline L1 184B, segments 190A and 190B and segments 192A and 192B. As can be seen in FIG. 13, segments 190A and 190B intersect, as do segments 192A and 192B. When tooth packing control module 24 finds these intersecting segments, it determines that the corresponding teeth intersect.

FIG. 14 shows an enlarged illustration of cross-section C3 (see FIG. 11B), polyline L0 183A, polyline L1 183B, intersecting line segments 194A and 194B and intersecting line segments 196A and 196B. Similarly, FIG. 15 shows an enlarged illustration of cross-section C0 (see FIG. 11B), polyline L0 180A, polyline L1 180B, intersecting line segments 198A and 198B. When tooth packing control module 24 finds these intersecting segments, it determines that the corresponding teeth intersect.

Referring again to FIG. 12, tooth packing control module 24 sets indices i and j to zero (210) for the first iteration. Tooth packing control module 24 next determines whether the current polyline segments $L0_i$ and $L1_j$ intersect (212). To do this, tooth packing control module 24 may use any of a number of different intersection detection methods. For example, tooth packing control module 24 may compare the equations describing the current line segments to determine whether they intersect. If the current segments do intersect, tooth packing control module 24 determines that the corresponding teeth intersect (228). In one embodiment, the process may finish (230) at this point. In another embodiment, tooth packing control module 24 may store the intersection information and continue checking all of the polylines for intersection, storing any relevant intersection information, until all of the polylines have been checked.

If the current segments do not intersect, tooth packing control module 24 increments j (214) and determines whether all segments on polyline L1 have been checked (216). If not, tooth packing control module 24 checks the current polyline segment $L0_i$ for intersection with the next polyline segment in polyline L1, $L1_j$. Tooth packing control module continues to increment j until all polyline segments $L1_j$ are checked for intersection with the current polyline segment $L0_i$. Then, tooth packing control module 24 resets j to 0 and increments i (218) to check the next segment on polyline L0. Tooth packing control module 24 continues the process until all segments in polyline L0 are checked with all segments in polyline L1 (220). Then, tooth packing control module 24 increments index k (222) to check the next cross-section $C_k$ (for example polyline C1 in FIG. 10B or FIG. 11B). If after checking all cross-sections $C_k$ for intersection (224) there are no intersecting polyline segments, tooth packing control module 24 determines that the teeth do not intersect (226). The process may then finish (230).

Client computing device 4 may move orthodontic objects along the virtual archwire within the 3D environment in accordance with the tooth packing algorithm described above. Client computing device may also move orthodontic objects in response to input from the orthodontic practitioner 8. In either case, to actually move the orthodontic objects along the virtual archwire, modeling software 20 may include some manner of representing (in other words, defining) the virtual archwire within the 3D environment. In one embodiment, the virtual archwire may be represented as a series of geometric segments. This method of representing the virtual archwire and corresponding method of moving an orthodontic object along a virtual archwire is described in copending and commonly assigned U.S. patent application Ser. No. 10/959,625, entitled "MOVEMENT OF ORTHODONTIC OBJECTS ALONG A VIRTUAL ARCHWIRE WITHIN A THREE-DIMENSIONAL (3D) ENVIRONMENT", 3M filed on evendate herewith to Raby, et al.

That application describes techniques for moving an orthodontic object (e.g., one or more orthodontic appliances and/or their associated teeth) from one position to another along a virtual archwire. In one embodiment, the application describes representing an archwire within a three-dimensional (3D) environment with a plurality of segments, receiving input indicative of movement of an orthodontic object along the archwire, and moving the orthodontic object within the 3D environment as indicated along the archwire based on the plurality of segments.

Various embodiments of the invention have been described. These and other embodiments are within the scope of the following claims.

The invention claimed is:

1. A method comprising:
   automatically determining positions of orthodontic objects along an archwire within a three-dimensional (3D) environment based on a proposed orthodontic prescription, wherein each of the orthodontic objects represents a tooth of patient's dental arch, and wherein the positions are determined such that the orthodontic objects do not intersect, wherein automatically determining positions of the orthodontic objects comprises:
   placing a first tooth within the 3D environment; and
   placing a second tooth within the 3D environment such that the second tooth is positioned within a desired tolerance of the first tooth, wherein placing the second tooth comprises:
   determining whether the first tooth and the second tooth intersect within the 3D environment;
   moving the second tooth in a mesial direction when the first tooth and the second tooth do not intersect; and
   moving the second tooth in a distal direction when the first tooth and the second tooth intersect; and
   displaying a digital representation of the orthodontic objects at the determined positions.

2. The method of claim 1, further comprising receiving the proposed orthodontic prescription from one of a practitioner or a database.

3. The method of claim 1, wherein the proposed orthodontic prescription includes a plurality of orthodontic appliances each associated with a different one of a plurality of teeth in a dental arch and an archwire received in a slot of each of the orthodontic appliances.

4. The method of claim 3 wherein the proposed orthodontic prescription includes a set of geometric attributes associated with each orthodontic appliance.

5. The method of claim 3 wherein the proposed orthodontic prescription includes relative positions and orientations of each of the orthodontic appliances with respect to the associated teeth.

6. The method of claim 3, wherein automatically determining positions of orthodontic objects comprises moving each of the plurality of orthodontic appliances and the associated plurality of teeth within the 3D environment relative to the archwire.

7. The method of claim 3, wherein the orthodontic appliance is selected from the set of an orthodontic bracket, a buccal tube, a sheath and a button.

8. The method of claim 1, wherein the proposed orthodontic prescription is received from a practitioner via a user interface.

9. The method of claim 1, wherein automatically determining positions of orthodontic objects further comprises placing subsequent teeth within the 3D environment such that each of the subsequent teeth is positioned within the desired tolerance of a previously placed tooth.

10. The method of claim 1, wherein placing a second tooth comprises placing the second tooth within the 3D environment a defined distance away from the first tooth, and wherein placing the second tooth further comprises moving the second tooth in a mesial direction one half the defined distance toward the first tooth when the first tooth and the second tooth do not intersect.

11. The method of claim 1, wherein placing a second tooth comprises placing the second tooth within the 3D environment a defined distance away from the first tooth, and wherein placing the second tooth further comprises moving the second tooth in a distal direction one half the defined distance away from the first toot when the first tooth and the second toot intersect.

12. The method of claim 1, wherein determining whether the first tooth and the second tooth intersect comprises:
   generating cross-sections of the first tooth and corresponding cross-sections of the second tooth;
   comparing each cross-section of the first tooth with the corresponding cross-section of the second tooth; and
   determining that the first tooth and the second tooth intersect if any cross-section of the first tooth intersects with the corresponding cross-section of the second tooth.

13. The method of claim 12, wherein the archwire defines an archwire plane, and wherein generating cross-sections of the first tooth and corresponding cross-sections of the second tooth comprises:
   defining a plurality of planes, wherein each of the planes is parallel to the archwire plane and wherein each of the planes intersects the first tooth and the second tooth in the 3D environment to produce cross-sections of the first tooth and the corresponding cross-sections of the second tooth.

14. A method comprising:
   automatically determining positions of orthodontic objects along an archwire within a three-dimensional (3D) environment based on proposed orthodontic prescription, wherein each of the orthodontic objects represents a tooth of patient's dental arch, wherein the positions are determined such that the orthodontic objects do not intersect, and wherein automatically determining positions of orthodontic objects comprises placing a first anterior-most tooth and placing a second anterior-most tooth within a desired tolerance of the first anterior-most tooth; and displaying a digital representation of the orthodontic objects at the determined positions.

15. A method comprising:

automatically determining positions of orthodontic objects along an archwire within a three-dimensional (3D) environment based on a proposed orthodontic prescription, wherein each of the orthodontic objects represents a tooth of patient's dental arch, and wherein the positions are determined such that the orthodontic objects do not intersect, wherein automatically determining positions of the orthodontic objects comprises:
  placing a first anterior-most tooth in a right quadrant of a dental arch a defined distance from a median line of an archwire; and
  placing a second anterior-most tooth in a left quadrant of the dental arch the defined distance from the median line of the archwire; and
  displaying a digital representation of the orthodontic objects at the determined positions.

16. The method of claim 15, further comprising:
determining whether the first anterior-most tooth in the right quadrant and the second anterior-most tooth in the left quadrant intersect;
moving the first anterior-most tooth in the right quadrant mesially toward the midline of the archwire and moving the second anterior-most tooth in the left quadrant mesially toward the midline of the archwire when the first anterior-most tooth in the right quadrant and the second anterior-most tooth in the left quadrant do not intersect; and
moving the first anterior-most tooth in the right quadrant distally away from the midline of the archwire and moving the second anterior-most tooth in the left quadrant distally away from the midline of the archwire when the first anterior-most tooth in the right quadrant and the second anterior-most tooth in the left quadrant intersect.

17. The method of claim 16, wherein moving the first anterior-most tooth in the right quadrant mesially toward the midline of the archwire and moving the second anterior-most tooth in the left quadrant mesially toward the midline of the archwire comprises moving the first anterior-most tooth in the right quadrant one half the defined distance mesially toward the midline of the archwire and moving the second anterior-most tooth in the left quadrant one half the defined distance mesially toward the midline of the archwire.

18. The method of claim 16, wherein moving the first anterior-most tooth in the right quadrant distally away from the midline of the archwire and moving the second anterior-most tooth in the right quadrant distally away from the midline of the archwire comprises moving the first anterior-most tooth in the right quadrant one half the defined distance distally away from the midline of the archwire and moving the second anterior-most tooth in the right quadrant one half the defined distance distally away from the midline of the archwire.

19. A system comprising:
a computing device; and
modeling software executing on the computing device, wherein the modeling software comprises:
  a tooth packing control module that automatically determines positions of orthodontic objects along an archwire within a three-dimensional (3D) environment based on a proposed orthodontic prescription, wherein each of the orthodontic objects represents a tooth of a patient's dental arch, and wherein the positions are determined such that the orthodontic objects do not intersect, and wherein the tooth packing control module:
    places a first tooth along an archwire in a first quadrant of the dental arch; and
    places a second tooth along the archwire in the first quadrant of the dental arch such that the first tooth and the second tooth are positioned within a desired tolerance of each other, wherein placing the second tooth comprises:
      determining whether the first tooth and the second tooth intersect;
      moving the second tooth in a mesial direction within the 3D environment when the first tooth and the second tooth do not intersect; and
      moving the second tooth in a distal direction within the 3D environment when the first tooth and the second tooth intersect; and
  a user interface that displays a digital representation of the orthodontic objects at the determined positions.

20. The system of claim 19, wherein the proposed orthodontic prescription includes a plurality of orthodontic appliances each associated with a different one of a plurality of teeth in the dental arch and an archwire received in a slot of each orthodontic appliance.

21. The system of claim 20 wherein the tooth packing control module automatically determines positions of subsequent teeth along the archwire based on the orthodontic prescription such that each subsequent tooth is positioned within the desired tolerance of a previously placed tooth.

22. The system of claim 20, wherein the orthodontic appliance comprises an orthodontic bracket, a buccal tube, a sheath or a button.

23. The system of claim 19, wherein the tooth packing control module places the second tooth along the archwire a defined distance away from the first tooth.

24. The system of claim 23, wherein the tooth packing control module moves the second tooth in a mesial direction one half the defined distance toward the first tooth.

25. The system of claim 23, wherein the tooth packing control module moves the second tooth in a distal direction one half the defined distance away from the first tooth.

26. The system of claim 19, further comprising a database to store the proposed orthodontic prescription.

27. The system of claim 26, wherein the database is located remote from the computing device and coupled to the computing device via a network.

28. The system of claim 19, wherein the user interface receives input from the practitioner regarding the proposed orthodontic prescription.

29. A computer-readable storage medium comprising instructions for causing a programmable processor to:
  automatically determine positions of orthodontic objects along an archwire within a three-dimensional (3D) environment based on a proposed orthodontic prescription, wherein each of the orthodontic objects represents a tooth of a patient's dental arch, and wherein the positions are determined such that the orthodontic objects do not intersect, wherein automatically determining positions of orthodontic objects comprises:
    placing a first tooth along an archwire in the 3D environment in a first quadrant of the dental arch; and placing a second toot along the archwire in the 3D environment in the first quadrant of the dental arch such that the first tooth and the second tooth are positioned within a desired tolerance of each other, wherein placing the second tooth comprises:

determining whether the first tooth and the second tooth intersect:

moving the second tooth in a mesial direction within the 3D environment when the first tooth and the second tooth do not intersect; and moving the second tooth in a distal direction within the 3D environment when the first tooth and the second tooth intersect; and display a digital representation of the orthodontic objects at the determined positions.

30. The computer-readable storage medium of claim 29, wherein the orthodontic objects comprise teeth.

31. The computer-readable storage medium of claim 29, wherein each of a plurality of teeth in the dental arch has an associated orthodontic appliance having a slot through which an archwire fits, and wherein the instructions cause the processor to automatically determining positions of teeth along the archwire based on the proposed orthodontic prescription such that a each of the teeth is placed within the desired tolerance of a previously placed tooth.

* * * * *

UNITED STATES PATENT AND TRADEMARK OFFICE
CERTIFICATE OF CORRECTION

PATENT NO. : 7,291,011 B2  Page 1 of 1
APPLICATION NO. : 10/959624
DATED : November 6, 2007
INVENTOR(S) : Nicholas A. Stark It is certified that error appears in the above-identified patent and that said Letters Patent is hereby corrected as shown below:

Column 14
Line 38, In Claim 11, delete "toot" and insert -- tooth --, therefor.
Line 39, In Claim 11, delete "toot" and insert -- tooth --, therefor.
Line 63, In Claim 14, after "on" insert -- a --.

Column 17
Line 1, In Claim 29, delete "toot" and insert -- tooth --, therefor.
Line 7, In Claim 29, after "intersect" delete ":" and insert -- ; --, therefor.

Column 18
Line 11, In Claim 31, after "that" delete "a".

Signed and Sealed this

Twenty-fifth Day of March, 2008

JON W. DUDAS
*Director of the United States Patent and Trademark Office*